(12) United States Patent
Robbins et al.

(10) Patent No.: US 9,642,921 B2
(45) Date of Patent: May 9, 2017

(54) CANCER COMBINATION THERAPY AND RECOMBINANT VECTORS

(71) Applicant: Tocagen Inc., San Diego, CA (US)

(72) Inventors: Joan M. Robbins, San Diego, CA (US); Douglas J. Jolly, Encinitas, CA (US); Derek G. Ostertag, San Diego, CA (US); Tiffany Huang, San Diego, CA (US); Harry E. Gruber, Rancho Santa Fe, CA (US)

(73) Assignee: Tocagen Inc., San Diego, CA (US)

( * ) Notice: Subject to any disclaimer, the term of this patent is extended or adjusted under 35 U.S.C. 154(b) by 327 days.

(21) Appl. No.: 14/137,803

(22) Filed: Dec. 20, 2013

(65) Prior Publication Data

US 2014/0178340 A1 Jun. 26, 2014

Related U.S. Application Data

(60) Provisional application No. 61/740,415, filed on Dec. 20, 2012.

(51) Int. Cl.
| | | |
|---|---|---|
| *A01N 63/00* | (2006.01) | |
| *A61K 48/00* | (2006.01) | |
| *A61K 31/495* | (2006.01) | |
| *A61K 31/513* | (2006.01) | |
| *A61K 38/50* | (2006.01) | |
| *A61K 35/768* | (2015.01) | |

(52) U.S. Cl.
CPC ........ *A61K 48/0058* (2013.01); *A61K 31/495* (2013.01); *A61K 31/513* (2013.01); *A61K 35/768* (2013.01); *A61K 38/50* (2013.01); *C12Y 305/04001* (2013.01); *C12N 2740/13032* (2013.01)

(58) Field of Classification Search
None
See application file for complete search history.

(56) References Cited

U.S. PATENT DOCUMENTS

| | | |
|---|---|---|
| 6,033,905 A | 3/2000 | Eiden et al. |
| 6,117,681 A | 9/2000 | Salmons et al. |
| 6,303,380 B1 | 10/2001 | Lin et al. |
| 6,410,313 B1 | 6/2002 | Kasahara et al. |
| 6,448,390 B1 | 9/2002 | Albritton et al. |
| 6,451,304 B1 | 9/2002 | Friedmann et al. |
| 6,576,463 B1 | 6/2003 | Kasahara et al. |
| 6,806,080 B2 | 10/2004 | Kasahara et al. |
| 6,899,871 B2 | 5/2005 | Kasahara et al. |
| 6,953,688 B2 | 10/2005 | Ferrick et al. |
| 7,056,730 B2 | 6/2006 | Pedersen et al. |
| 7,790,445 B2 | 9/2010 | Erbs |
| 2002/0068362 A1 | 6/2002 | Murray et al. |
| 2002/0137889 A1 | 9/2002 | Soong et al. |
| 2003/0003565 A1 | 1/2003 | Dubensky |
| 2003/0121068 A1 | 6/2003 | Orchard et al. |
| 2003/0157070 A1 | 8/2003 | Jolly |
| 2003/0157718 A1 | 8/2003 | Pedersen et al. |
| 2003/0165466 A1 | 9/2003 | Gromeier et al. |
| 2003/0219410 A1 | 11/2003 | Calatrava |
| 2004/0068762 A1 | 4/2004 | Attar et al. |
| 2004/0096972 A1 | 5/2004 | Audit et al. |
| 2004/0142449 A1 | 7/2004 | Tonjes et al. |
| 2004/0146489 A1 | 7/2004 | Yu et al. |
| 2004/0197308 A1 | 10/2004 | Takahashi et al. |
| 2004/0248827 A1 | 12/2004 | Zheng et al. |
| 2005/0002903 A1 | 1/2005 | Kasahara et al. |
| 2005/0059004 A1 | 3/2005 | Atabekov et al. |
| 2005/0063945 A1 | 3/2005 | Paul |
| 2007/0003522 A1 | 1/2007 | Albritton |
| 2007/0254357 A1 | 11/2007 | Gregory et al. |
| 2007/0264235 A1 | 11/2007 | Erbs |
| 2008/0008685 A1 | 1/2008 | Kasahara |
| 2008/0227736 A1 | 9/2008 | Chen et al. |
| 2009/0169580 A1 | 7/2009 | Whelan et al. |
| 2010/0330051 A1 | 12/2010 | Erbs |
| 2011/0287020 A1* | 11/2011 | Gruber ............... A61K 38/2292 424/155.1 |
| 2012/0052554 A1 | 3/2012 | Kasahara et al. |
| 2014/0178340 A1* | 6/2014 | Robbins ............. A61K 48/0058 424/93.2 |

FOREIGN PATENT DOCUMENTS

| | | |
|---|---|---|
| WO | 9920742 A2 | 4/1999 |
| WO | 9936561 A1 | 7/1999 |
| WO | 0104266 A1 | 1/2001 |
| WO | 2006127980 A2 | 11/2006 |
| WO | 2007095201 A2 | 8/2007 |
| WO | 2007107156 A2 | 9/2007 |
| WO | 2008151633 A2 | 12/2008 |
| WO | 2010002937 A1 | 1/2010 |
| WO | 2010036986 A2 | 4/2010 |
| WO | 2010045002 A2 | 4/2010 |
| WO | 2011126864 A2 | 10/2011 |
| WO | 2012021794 A1 | 2/2012 |

OTHER PUBLICATIONS

Carlson, B. et al., "Radiosensitizing effects of Temozolomide Observed In Vivo Only in a Subset of O6-methylguanine-DNA Methyltransferase Methylated Glioblastoma Multiforme Xenografts", Int. J. Radiation Oncology Biol. Phys., 2009, vol. 75: pp. 212-219.*

(Continued)

*Primary Examiner* — Michael Burkhart
(74) *Attorney, Agent, or Firm* — Joseph R. Baker, Jr.; Gavrilovich, Dodd & Lindsey LLP

(57) ABSTRACT

This disclosure relates to a combination therapy of chemotherapeutics and/or radiosensitizing agents with a replication competent viral vectors for treating cell proliferative disorders and chemotherapeutic treatments. The disclosure further relates to the use of such replication competent viral vectors for delivery and expression of a heterologous nucleic acid in normal and diseased tissues and methods and compositions that facilitate such delivery and expression to tissues in vivo and in vitro. The disclosure further relates to replication competent retroviral vectors for these uses and in conjunction with methods and compositions that facilitate in vivo therapeutics.

14 Claims, 5 Drawing Sheets

(56) References Cited

OTHER PUBLICATIONS

Clarke, J. et al., "Randomized Phase II Trial of Chemotherapy Followed by Either Dose-Dense or Metronomic Temozolomide for Newly Diagnosed Glioblastoma", 2009, J. Clin. Oncol., vol. 27: pp. 3861-3867.*

Aagaard et al., "Fv1-like restriction of N-tropic replication-competent murine leukaemia viruses in mCAT-1-expressing human cells," Journal of General Virology 83:439-442 (2002).

Addison et al., "Comparison of the human versus murine cytomegalovirus immediate early gene promoters for transgene expression by adenoviral vectors," J. Gen. Virol. 78:1653-1661 (1997).

Aghi et al., "Synergistic Anticancer Effects of Ganciclovir/Thymidine Kinase and 5-Fluorocytosine/Cytosine Deaminase Gene Therapies", J. Natl. Cancer Inst. 90(5):370-380 (1998).

Akbulut et al., "Cytotoxic effect of replication-competent adenoviral vectors carrying L-plastin promoter regulated E1A and cytosine deaminase genes in cancers of the breast, ovary, and colon," Cancer Gene Therapy 10:388-395 (2003).

Akbulut et al., "Vector targeting makes 5-fluorouracil chemotherapy less toxic and more effective in animal models of epithelial neoplasms," 10(22):7738-46 (2004).

Akimoto, M. et al., A new delivery system for 5-fluorouracil using prodrug and converting enzyme; Laboratory Science; Br J Ophthalmol 2002;86:581-586; www.bjophthalmol.com.

Ambrose et al., "In vitro characterization of a simian immunodeficiency virus human immunodeficiency virus (HIV) chimera expressing HIV type 1 reverse transcriptase to study antiviral resistance in pigtail macaques," J. Virol. 78:13553-13561 (2004).

Anello et al., "Adenovirus Mediated Cytosine Deaminase Gene Transduction and 5-fluorocytosine Therapy Sensitizes Mouse Prostate Cancer to Irradiation," The Journal of Urology 164(6):2173-2177 (2005).

Arrigo et al., "Regulation of Rous sarcoma virus RNA splicing and stability," Mol. Cell Biol. 8:4858-4867 (1988).

Attar et al., "Transgenic Non-Human Mammals Expressing a Reporter Nucleic Acid Under the Regulation of Androgen Response Elements", May 20, 2004, Score Result.

Bachrach et al., "Efficient Gene Transfer into Spleen Cells of Newborn Mice by a Replication-Competent Retroviral Vector," 293(2):328-334 (2002).

Bachrach et al., "In Vivo Infection of Mice by Replication-Competent MLV-Based Retrovirus Vectors," Methods in Molecular Medicine 76:343-352 (2003).

Baranick et al., "Splicing mediates the activity of four putative cellular internal ribosome entry sites," PNAS 105 (12):4733-4738 (2008).

Barsov et al., "Adaptation of chimeric retroviruses in vitro and in vivo: isolation of avian retroviral vectors with extended host range," J. Virol. 75:4973-4983 (2001).

Beijer, Gijsbertus. International Preliminary Report on Patentability. International Application No. PCT/US2009/058510. Date of mailing: Apr. 7, 2011.

Beijer, Gijsbertus. International Preliminary Report on Patentability. International Application No. PCT/US2009/058512. Date of Mailing: Apr. 7, 2011.

Bhattacharyya, Madhumita, "Gene therapy developments for pancreatic cancer," Best Pract. & Res. Clin. Gastro., 20(2):285-298, 2006.

Blackburn et al., "Adenovrial transduction of a cytosine deaminase/thymidine kinase fusion gene into prostate carcinoma cells enhances prodrug and radiation sensitivity," International Journal of Cancer 82(2):293-297 (1999).

Bourbeau et al., "Suicide gene therapy with an adenovirus expressing the fusion gene CD::UPRT in human glioblastomas: different sensitivities correlate with p53 status," The Journal of Gene Medicine 6:1320-1332 (2004).

Bourbeau et al., "Improvement of antitumor activity by gene amplification with a replicating but nondisseminating adenovirus," Cancer Research, 67(7):3387-95 (2007).

Bunnell et al., "Transplantation of transduced nonhuman primate CD34+ cells using a gibbon ape leukemia virus vector: restricted expression of the gibbon ape leukemia virus receptor to a subset of CD34+ cells," Gene Ther. 6:48-56 (1999).

Chang et al., "A Replication-Competent Feline Leukemia Virus, Subgroup A (FELV-A), Tagged with Green Fluorescent Protein Reporter Exhibits In Vitro Biological Properties Similar to Those of the Parental FeIV-A," Journal of Virology 75(18):8837-8841 (2001).

Cherry et al., "Retroviral Expression in Embryonic Stem Cells and Hematopoietic Stem Cells," Molecular and Cellular Biology 20(20):7419-7426 (2000).

Chio, Jun Ho. International Search Report and Written Opinion. International Application No. PCT/US2009/058510. Date of mailing of the International Search Report Jul. 6, 2010.

Cho, Jeong Han. International Search Report and Written Opinion. International Application No. PCT/US2009/058512. Date of mailing of the Report: May 11, 2010.

Coulombe et al., "A replication-competent promoter-trap retrovirus," J. Virol. 70:6810-6815 (1996).

Cupelli et al., "Transcriptional initiation and postinitiation effects of murine leukemia virus long terminal repeat R-region sequences," J. Virol. 65:6961-6968 (1991).

Cupelli et al., "The secondary structure of the R region of a murine leukemia virus is important for stimulation of long terminal repeat-driven gene expression," J. Virol. 72:7807-7814 (1998).

Delassus et al., "Genetic organization of gibbon ape leukemia virus," Virology 173:205-213 (1989).

Delviks, Krista Anda., "Development of murine leukemia virus-based vectors for more effective gene therapy: genetic analysis of direct repeat deletions," Dissertation, West Virginia (1999).

Dias et al., "Targeted chemotherapy for head and neck cancer with a chimeric oncolytic adenovirus coding for bifunctional suicide protein FCU1," Clin. Cancer Res. 16(9):2540-9; 2010.

Diaz et al., "Exchange of viral promoter/enhancer elements with heterologous regulatory sequences generates targeted hybrid long terminal repeat vectors for gene therapy of melanoma," J. Virol. 72:789-795 (1998).

Dillon et al., "Construction of a replication competent murine retrovirus vector expressing the human immunodeficiency virus type 1 Tat transactivator protein," J. Virol. 65:4490-4493 (1991).

Donahue et al., "Helper virus induced T cell lymphoma in nonhuman primates after retroviral mediated gene transfer," J. Expt. Med. 176:1125-1135 (1992).

Duch et al., "Transgene stability for three replication-competent murine leukemia virus vectors," Gene 329:61-69 (2004).

Edelstein et al., "Gene therapy clinical trials worldwide 1989-2004—an overview," J. Gene Med. 6:597-602 (2004).

Erbs, P., et al., Characterization of the *Saccharomyces cerevisiae* FCY1 gene encoding cytosine deaminase and its homologue FCA1 of Candida albicans; Curr Genet 31: 1-6; Springer-Verlag 1997.

Erbs, Gene-Bank-AAG33626; cytosine deaminase-uracil phosphoribosyltransferase fusion protein [synthetic construct]; Gene-Bank-AAG33626; pp. 1-2; http://www.ncbi.nlm.nih.gov/protein/AAg33626.

Erbs et al., "In Vivo Cancer Gene Therapy by Adenovirus-mediated Transfer of a Bifunctional Yeast Cystosine Deaminase/Uracil Phosphoribosyltransferase Fusion Gene," Cancer Research 60(14):3813-3822 (2000).

Erbs et al. "Modified vaccinia virus Ankara as a vector for suicide gene therapy," Cancer Gene Ther. 15(1):18-28 (2008).

Erlwein et al., "The proline-rich region of the ecotropic Moloney murine leukaemia virus envelope protein tolerates the insertion of the green fluorescent protein and allows the generation of replication-competent virus," J. Gen. Virol. 84:369-373 (2003).

Ernst et al., "A structured retroviral RNA element that mediates nucleocytoplasmic export of intron containing RNA", Mol. Cell. Biol., 17:135-144 (1997).

(56) References Cited

OTHER PUBLICATIONS

Evans et al., "A neutralizable epitope common to the envelope glycoproteins of ecotropic, polytropic, xenotropic, and amphotropic murine leukemia viruses," J. Virol. 64: 6176-6183 (1990).
Ferrick et al., "Vector for screening for modulators of IgE synthesis, secretion and switch rearrangement", Score Result, Sequence 5 from patent 6953688.
Finger et al., "Replicating retroviral vectors mediating continuous production and secretion of therapeutic gene products from cancer cells," Cancer Gene Ther. 12:464-474 (2005).
Fischer et al., "Mechanisms of thymidine kinase/ganciclovir and cytosine deaminase/5-fluorocytosine suicide gene therapy-induced cell death in glioma cells," Oncogene 24:1231-1243 (2005).
Fogar, P. et al., "Suicide Gene Therapy With the Yeast Fusion Gene Cytosine Deaminase/Uracil Phosphoribosyltransferase Is Not Enough for Pancreatic Cancer", Pancreas, vol. 35, No. 3, Oct. 2007.
Foloppe et al., "Targeted delivery of a suicide gene to human colorectal tumors by a conditionally replicating vaccinia virus," Gene Ther. 15(20):1361-71 (2008).
Freytag et al., "Phase I Study of Replication-competent Adenovirus-mediated Double Suicide Gene Therapy for the Treatment of Locally Recurrent Prostate Cancer," Cancer Res. 62:4968-4976 (2002).
Miller et al., "Intratumurol 5-Fluorouracil Produced by Cytosine Deaminase/5-Fluorocytosine Gene Therapy Is Effective for Experimental Human Glioblastomas," Cancer Res. 62:773-780 (2002).
Morgan et al., "Retroviral vectors containing putative internal ribosome entry sites: development of a polycistronic gene transfer system and applications to human gene therapy," Nucleic Acids Research 20(6):1293-1299 (1992).
Mullen et al., "Transfer of the bacterial gene for cytosine deaminase to mammalian cells confers lethal sensitivity to 5-fluorocytosine: a negative selection system," PNAS 89(1):33-37 (1992).
Mukesh et al., "High and Selective Expression of Yeast Cytosine Deaminase Under a Carcinoembryonic Antigen Promoter-Enhancer," Cancer Res. 62:2337-2342 (2002).
Murakami et al., "High-level expression of exogenous genes by replication-competent retrovirus vectors with an internal ribosomal entry site," Gene 202:23-29 (1997).
Nack et al., "Replacement of the murine leukemia virus (MLV) envelope gene with a truncated HIV envelope gene in MLV generates a virus with impaired replication capacity," Virology 315:209-216 (2003).
Nakamura et al., "Multimodality Therapy with a Replication-conditional Herpes Simplex Virus 1 Mutant that Expresses Yeast Cytosine Deaminase for intratumoral Conversion of 5-Fluorocytosine to 5-Fluorouracil," Cancer Res. 61:5447-5452 (2001).
Naldini et al., "Efficient transfer, integration, and sustained long-term expression of the transgene in adult rat brains injected with a lentiviral vector," Proc. Natl. Acad. Sci. USA 93:11382-11388 (1996).
Negroni et al., "Treatment of colon cancer cells using the cytosine deaminase/5-fluorocytosine suicide system induces apotosis, modulation of the proteome, and Hsp90B phsophorylation," Molecular Cancer Therapeutics 6:2747-2756 (2007).
Nishiyama, T. et al., Antineoplastic Effects in Rats of 5-Fluorocytosine in Combination with Cytosine Deaminase Capsules; Cancer Res 1985;45:1753-1761.
Nogues et al., "Transcriptional activators differ in their abilities to control alternative splicing," J. Biol. Chem. 277:43110-43114 (2002).
Nyati, M. et al., "High and Selective Expression of Yeast Cytosine Deaminase under a Carcinoembryonic Antigen Promoter-Enhancer," Cancer Res. 2002;62:2337-2342.
O'Reilly et al., "Second-site changes affect viability of amphotropic/ecotropic chimeric enveloped murine leukemia viruses," J. Virol. 74:899-913 (2000).
Overbaugh et al., "Receptors and entry cofactors for retroviruses include single and multiple transmembrane-spanning proteins as well as newly described glycophosphatidylinositol-anchored and secreted proteins," Microbiol. Mol. Biol. Rev. 65:371-389 (2001).
Owens et al., "Human and simian immunodeficiency virus capsid proteins are major viral determinants of early, postentry replication blocks in simian cells," J. Virol. 77:726-731 (2003).
Paar et al., "Effects of Viral Strain, Transgene Position, and Target Cell Type on Replication Kinetics, Genomic Stability and Transgene Expression of Replication-Competent Murine Leukemia Virus-Based Vectors," Journal of Virology 81(13):6973-6983 (2007).
Paar et al., "Influence of vector design and host cell on the mechanism of recombination and emergence of mutant subpopulations of replicating retroviral vectors," BMC Molecular Biology 10(8) (2009).
Pao et al., "Use of avian retroviral vectors to introduce transcriptional regulators into mammalian cells for analyses of tumor maintenance," PNAS 100(15):8764-8769.
Paola et al., "Suicide Gene Therapy With the Yeast Fusion Gene Cytosine Deaminase/Uracil Phosphoribosyltransferase is Not Enough for Pancreatic Cancer," Pancreas 35(3):224-231 (2007).
Poltoratsky, V. "Recombiongenic Phenotype of Human Activation-Induced Cytosine Deaminas," J. Immunol. 2004; 172:4308-4313.
Poon et al. "Nucleocapsid and matrix protein contributions to selective human immunodeficiency virus type 1 genomic RNA packaging," J. Virol. 72:1983-1993 (1998).
Portsmouth et al., "Suicide genes for cancer thearpy," Mol. Aspects of Med. 28:4-41, 2007.
Qiao et al. "VSV-G pseudotyped, MuLV-based, semi-replication-competent retrovirus for cancer treatment. Gene Ther," 13:1457-1470 (2006).
Rainov et al., "Clinical trials with retrovirus mediated gene therapy—what have we learned?," J. Neurooncol. 65:227-236 (2003).
Reik et al., Replication-competent Moloney murine leukemia virus carrying a bacterial suppressor tRNA gene: selective cloning of proviral and flanking host sequences. Proc. Natl. Acad. Sci. USA 82:1141-1145 (1985).
Robson et al., "Selection of optimal polypurine tract region sequences during Moloney murine leukemia virus replication," J. Virol. 74:10293-10303 (2000).
Roscigno et al., "A mutational analysis of the polypyrimidine tract of introns. Effects of sequence differences in pyrimidine tracts on splicing," J. Biol. Chem. 268:11222-11229 (1993).
Saavedra et al., "The simian retrovirus-1 constitutive transport element, unlike the HIV-1 RRE, uses factors required for cellular mRNA export," Curr. Biol. 7:619-628 (1997).
Sanders, D. A. "No false start for novel pseudotyped vectors," Curr. Opin. Biotechnol. 13, 437-442 (2002).
Schulz, Regine, "Supplemental European Search Report", EP09820986, European Patent Office, Oct. 28, 2011.
Segall et al., "Characterization and Detection of Artificial Replication-Competent Lentivirus of Altered Host Range," Molecular Therapy 8:118-129 (2003).
Shen, H. et al., "Targeting of the Activation-Induced Cytosine Deaminase Is Strongly Influenced by the Sequence and Structure of the Targeted DNA"; Molecular and Cellular Biology, Dec. 2005, p. 10815-10821 vol. 25, No. 24.
Shikova-Lekova et al. "Replication-competent hybrids between murine leukemia virus and foamy virus," J. Virol. 77, 7677-7681 (2003).
Shin et al., "Replication of lengthened Moloney murine leukemia virus genomes is impaired at multiple stages," J. Virol. 74:2694-2702 (2000).
Short et al., "Correlation of leukemogenic potential of murine retroviruses with transcriptional tissue preference of the viral long terminal repeats," J. Virol. 61:1067-1072 (1987).
Sliva et al., "Stable integration of a functional shRNA expression cassette into the murine leukemia virus genome," Virology 351(1):218-225 (2006).

(56) References Cited

OTHER PUBLICATIONS

Sodroski et al., "Repetitive structure in the long-terminal-repeat element of a type II human T-cell leukemia virus," Proc. Natl. Acad. Sci. USA 81:4617-4621,1984.
Soifer et al., "A Novel, Helper-Dependent, Adenovirus-Retrovirus Hybrid Vector: Stable Transduction by a Two-Stage Mechanism," Molecular Therapy 5(5):599-608 (2002).
Solly et al., "Replicative retroviral vectors for cancer gene therapy," Cancer Gene Ther. 10:30-39 (2003).
Sotos, G. et al., "Preclinical and clinical aspects of biomodulation of 5-fluorouracil"; Cancer Treatment Reviews (1994) 20, 11-49.
Staffa et al., Identification of positive and negative splicing regulatory elements within the terminal tat-rev exon of human immunodeficiency virus type 1. Mol. Cell Biol. 15:4597-4605 (1995).
Stolworthy, T., et al., "Yeast Cytosine Deaminase Mutants with Increased Thermostability Impart Sensitivity to 5-Fluorocytosine"; J Mol Biol. Mar. 28, 2008; 377(3): 854-869.
Stuhlmann et al., "Construction and properties of replication-competent murine retroviral vectors encoding methotrexate resistance," Mol. Cell. Biol. 9:100-108 (1989).
Subramanian et al., "Temperature-sensitive replication-competent adenovirus shRNA vectors to study cellular genes in virus-induced apoptosis," Methods in Molecular Medicine 130:125-134 (2007).
Sun et al., "Chronic gene delivery of interferon-inducible protein 10 through replication competent retrovirus vectors suppresses tumor growth," Cancer Gene Ther. 12:900-912 (2005).
Svarovskaia et al., "Retroviral mutation rates and reverse transcriptase fidelity," Front. Biosci. 8:d117-d134 (2003).
Swanstrom et al., "Synthesis, assembly, and processing of viral proteins," In Retroviruses (Coffin, J. M., Hughes, S. H. & Varmus, H., eds), pp. 263-334, (1997).
Tai et al., "Antibody-Mediated Targeting of Replication-Competent Retroviral Vectors," Human Gene Therapy 14:789-802 (2003).
Tai et al., "Single-Shot, Multicycle Suicide Gene Therapy by Replication-Competent Retrovirus Vectors Achieves Long-Term Survival Benefit in Experimental Glioma," Molecular Therapy 12(5):842-851 (2005).
Tai et al., "Replication-competent retrovirus vectors for cancer gene therapy," Frontiers in Bioscience 13:3083-95 (2008).
Takeuchi et al., "Type C retrovirus inactivation by human complement is determined by both the viral genome and the producer cell," J. Virol. 68: 8001-8007 (1994).
Trubetskoy et al., "R region sequences in the long terminal repeat of a murine retrovirus specifically increase expression of unspliced RNAs," J. Virol. 73:3477-3483 (1999).
Valsamakis et al., The human immunodeficiency virus type 1 polyadenylylation signal: a 3' long terminal repeat element upstream of the AAUAAA necessary for efficient polyadenylylation, Proc. Natl. Acad. Sci. USA 88:2108-2112 (1991).
Van Santen et al., "mRNA precursor splicing in vivo: sequence requirements determined by deletion analysis of an intervening sequence," Proc. Natl Acad. Sci. USA 82:2885-2889 (1985).
Wallace, P. et al., Intratumoral Generation of 5-Fluorouracil Mediated by an Antibody-Cytosine Deaminase Conjugate in Combination with 5-Fluorocytosine; Cancer Res, 1994;54:2719-2723.
Wang et al., "Highly Efficient and Tumor-Restricted Gene Transfer to Malignant Gliomas by Replication-Competent Retroviral Vectors," Human Gene Therapy 14:117-127 (2003).
Wang et al., "A murine leukemia virus with Cre-LoxP excisible coding sequences allowing superinfection, transgene delivery, and generation of host genomic deletions," Retrovirology 1(5) (2004).
Wang, W. et al., "Use of replication-competent retroviral vectors in an immunocompetent intracranial glioma model", Neurosurg. Focus, vol. 20; Apr. 2006; pp. 1-9.
Warmann et al., "Adenovirus-mediated cytosine deaminase/5-fluorocytosine suicide gene therapy of human hepatoblastoma in vitro," Pediatric Blood & Cancer, 53: 145-151 (2009).
Xie et al., "Adenovirus-mediated tissue-targeted expression of a caspase-9-based artificial death switch for the treatment of prostate cancer," Cancer Res. 61:6795-6804 (2001).
Xie et al., "Enhanced Retinal Ganglion Cell Differentiation by ath5 and NSCL1 Coexpression," IOVS 45(9):2922-2928 (2004).
Yamashita et al., "The cell cycle independence of HIV infections is not determined by known karyophilic viral elements," PLoS Pathog. 1:e18 (2005).
Yap et al., "Trim5alpha protein restricts both HIV-1 and murine leukemia virus," Proc. Natl. Acad. Sci. USA 101:10786-10791 (2004).
Yi, et al., "Retroviral gene therapy: safety issues and possible solutions," Curr. Gene Ther. 5:25-35 (2005).
Yin et al., "Insertion of sequences into the 3' untranslated region of a replication-competent spleen necrosis virus vector disrupts env gene expression," Arch Virol (1999) 144:73-87.
Young et al., "Chimeric Retroviral Helper Virus and Picornavirus IRES Sequence to Eliminate DNA Methylation for Improved Retroviral Packaging Cells," J. Virol. 74(11):5242-5249 (2000).
Young, Lee W. International Search Report and Written Opinion. International Application No. PCT/US2009/049322. Date of mailing: Sep. 2, 2009.
Zhang, J., et al., "A Novel Oncolytic Adenovirus Expressing *Escherichia coli* Cytosine Deaminase Exhibits Potent Antitumor Effect on Human Solid Tumors"; Cancer Biotherapy and Radiopharmaceuticals; vol. 25, No. 4, 2010; pp. 487-495.
Friedmann et al., "Method for Retrovirus Vector Production by Separated GAG and POL Expression", Score Result, U.S. Pat. No. 6,451,304, Sep. 17, 2002.
Garton et al., "Efficient Expression of Exogenous Genes in Primary Vascular Cells Using IRES-Based Retroviral Vectors," Biotechniques 32:830-843 (2002).
Giffo-Schmitt, Beate. International Preliminary Report on Patentability. International Application No. PCT/US2009/049322. Date of Issuance of Report: Jan. 5, 2011.
Guffey et al., "Engineered herpes simplex virus expressing bacterial cytosine deaminase for experimental therapy for brain tumors," Cancer Gene Therapy 14(1):45-56 (2007); Epub Sep. 22, 2006.
Guo et al., "Protein tolerance to random amino acid change", PNAS, Jun. 22, 2004, vol. 101, No. 25, 9205-9210.
Hacein-Bey-Abina et al., "LMO2-associated clonal T cell proliferation intwo patients after gene therapy for SCID-X1," Science 302:415-419 (2003).
Hiavaty et al., "Effects of sequences of prokaryotic origin on titer and transgene expression in retroviral vectors," Virology 330:351-360 (2004).
Hiraoka et al., "Tumor-Selective Gene Expression in a Hepatic Metastasis Model after Locoregional Delivery of a Replication-Competent Retrovirus Vector," Clin. Cancer Res. 12(23):7108-7116 (2006).
Hiraoka et al., "Vector-Mediated Suicide Gene Therapy in a Multifocal Therapeutic Efficacy of Replication-Competent Retrovirus Vector-Mediated Suicide Gene Therapy in a Multifocal Colorectal Cancer Metastasis Model," Cancer Research 67(11):5345-5353 (2007).
Hirschowitz et al., "In vivo adenovirus-mediated gene transfer of the *Escherichia coli* cytosine deaminase gene to human colon carcinoma-derived tumors induces chemosensitivity to 5-fluorocytosine," Hum. Gene Ther. 6(8):1055-63 (1995).
Horn et al., "Highly efficient gene transfer into baboon marrow repopulating cells using GALV-pseudotype oncoretroviral vectors produced by human packaging cells," Blood 100:3960-3967 (2002).
Huber et al., "Metabolism of 5-fluorocytosine to 5-fluorouracil in human colorectal tumor cells transduced with the cytosine deaminase gene: significant antitumor effects when only a small percentage of tumor cells express cytosine deaminase," PNAS 91(17):8302-8306 (1994).
Hughes, Stephen H., "The RCAS Vector System," Folia Biologica (Praha) 50(3-4):107019 (2004).
Ireton, G. et al., "The Structure of *Escherichia coli* Cytosine Deaminase", J. Mol. Biol. (2002) 315, 687-697.
Ireton, G. et al., "The 1.14A° Crystal Structure of Yeast Cytosine Deaminase: Evolution of Nucleotide Salvage Enzymes and Implications for Genetic Chemotherapy", Structure, vol. 11, 961-972, Aug. 2003.

(56) References Cited

OTHER PUBLICATIONS

Jespersen et al., "Expression of heterologous genes from an IRES translational cassette in replication competent murine leukemia virus vectors," Gene 239(2):227-235 (1999).
Johann et al., "Definition of a domain of GLVR1 which is necessary for infection by gibbon ape leukemia virus and which is highly polymorphic between species," J. Virol. 67:6733-6736 (1993).
Kaliberov et al., "Mutation of *Escherichia coli* cytosine deaminase significantly enhances molecular chemotherapy of human glioma," Gene Ther. 14(14):1111-9; 2007.
Kaliberova et al., "Molecular chemotherapy of pancreatic cancer using novel mutant bacterial cytosine deaminase gene," 7(9):2845-54 (2008).
Kasahara, N., "Viral Vectors", Score Results, U.S. Appl. No. 11/805,411, filed Jun. 7, 2007.
Kawasaki et al., "Replication-competent retrovirus vector-mediated prodrug activator gene therapy in experimental models of human malignant mesothelioma," Cancer Gene Therapy 18:571-578 (2011).
Kern, L et al., "The FUR1 gene of *Saccharomyces cerevisiae*: cloning, structure and expression of wild-type and mutant alleles", Gene, 88 (1990) 149-157; 1990.
Khatri et al., "Combination of cystosine deaminase with uracil phosphribosyl transferase leads to local and distant bystander effects against RM1 prostate cancer in mice", J. of Gene Medicine, 8:1086-1096, Jul. 11, 2006.
Kikuchi et al., "Highly Efficient Gene Delivery for Bladder Cancers by Intravesically Administered Replication-Competent Retroviral Vectors," Clin. Cancer Res. 13:4511-4518 (2007).
Klein et al., "Rapid identification of viable retrovirus-transduced cells using the green fluorescent protein as a marker," Gene Ther. 4:1256-1260 (1997).
Korkegian et al., "Chain A, Yeast Cytosine Deaminase Triple Mutant", Gene-Bank-Y1SB__A, pp. 1-2; http://www.ncbi.nlm.nih.gov/protein/1ySB_A.
Korkegian, A. et al., "Computational Thermostabilization of an Enzyme"; Science vol. 308; May 6, 2005; 857-860; www.sciencemag.org.
Kornblihtt et al., "Multiple links between transcription and splicing," RNA 10:1489-1498 (2004).
Kurozumi et al., "Apotosis Induction With 5-Fluorocytosine/Cytosine Deaminase gene therapy for Human Malignant Glioma Cells Mediated by Adenovirus," Journal of Neuro-Oncology 66(1-2):117-127 (2004).
Lazo et al., "Splice acceptor site for the env message of Moloney murine leukemia virus," J. Virol. 61:2038-2041 (1987).
Lesk et al., "Prediction of Protein Function from Protein Sequence and Structure", pp. 27 and 28, downloaded Sep. 16, 2007.
Lipinski et al., "Optimization of a synthetic beta-catenin-dependent promoter for tumor-specific cancer gene therapy," Mol. Ther. 10:150-161 (2004).
Liu et al., "Tumor-specific therapeutic effect induced by an oncolytic adenoviral vector containing heat shock protein 70 and prodrug activation genes," Gene Therapy, 13(16):1235-43.
Liu et al. "Engineering conditionally replication-competent adenoviral vectors carrying the cytosine deaminase gene increases the infectivity and therapeutic effect for breast cancer gene therapy," Cancer Gene Therapy, 13(4):346-56 (2006).
Liu et al., "The receptors for gibbon ape leukemia virus and amphotropic murine leukemia virus are not downregulated in productively infected cells," Retrovirology 8:53 (2011).
Logg et al., "A Uniquely Stable Replication-Competent Retrovirus Vector Achieves Efficient Gene Delivery in Vitro and in Solid Tumors," Human Gene Therapy 12:921-932 (2001).
Logg et al., "Genomic Stability of Murine Leukemia Viruses Containing Insertions at the Env-3' Untranslated Region Boundary," Journal of Virology 75(15):6989-6998 (2001).
Logg et al., "Tissue-Specific Transcriptional Targeting of a Replication-Competent Retroviral Vector," Journal of Virology 76(24):12783-12791 (2002).
Logg et al., "Retrovirus-Mediated Gene Transfer to Tumors," Methods in Molecular Biology 246:499-525 (2004).
Lu et al., "Highly efficient gene transfer to solid tumors in vivo by tumor-selective replicating retrovirus vectors," Int. J. Mol. Med. 25(5):769-75 (2010).
Maguire, Simon, Examination Report. New Zealand Application No. 592070. Date of Report: May 24, 2011.
Mahan, S. et al., "Random mutagenesis and selection of *Escherichia coli* cytosine deaminase for cancer gene therapy", Protein Engineering, Design & Selection vol. 17 No. 8 pp. 625-633, 2004.
Mahan, S. et al., "Alanine-Scanning Mutagenesis Reveals a Cytosine Deaminase Mutant with Altered Substrate Preference", Biochemistry 2004, 43, 8957-8964.
Malim et al., "The HIV-1 rev trans-activator acts through a structured target sequence to activate nuclear export of unspliced viral mRNA," Nature 338:254-257 (1989).
Marzio et al., "In vitro evolution of a highly replicating, doxycycline-dependent HIV for applications in vaccine studies," Proc. Natl Acad. Sci. USA 98:6342-6347 (2001).
Mechold et al., "Codon optimization of the BirA enzyme gene leads to higher expression and an improved efficiency of biotinylation of target proteins in mammalian cells", Journal of Biotechnology 116 (2005) 245-249.
Metzl et al., "Tissue- and Tumor-Specific Targeting of Murine Leukemia Virus-Based Replication-Competent Retroviral Vectors," Journal of Virology 80(14):7070-7078 (2006).
Mild et al., "Frequent intrapatient recombination between human immunodeficiency virus type 1 R5 and X4 envelopes: implications for coreceptor switch," J. Virol. 81:3369-3376 (2007).
Miller et al., "Gene transfer by retrovirus vectors occurs only in cells that are actively replicating at the time of infection," Mol. Cell. Biol. 10:4239-4242 (1990).
Miller et al., "Construction and properties of retrovirus packaging cells based on gibbon ape leukemia virus," J. Virol. 65:2220-2224 (1991).
Heo, Joo Hyung, International Search Report and Written Opinion, PCT/US2013/066709, Korean Intellectual Property Office, Date of Mailing: Jan. 28, 2014.

* cited by examiner

CANCER COMBINATION THERAPY AND RECOMBINANT VECTORS

CROSS REFERENCE TO RELATED APPLICATIONS

This application claims priority to U.S. Provisional Application Ser. No. 61/740,415, filed Dec. 20, 2012, the disclosure of which is incorporated herein by reference.

TECHNICAL FIELD

This disclosure relates to replication competent viral vectors for treating cell proliferative disorders and chemotherapeutic treatments. The disclosure further relates to the use of such replication competent viral vectors for delivery and expression of a heterologous nucleic acid in normal and diseased tissues and methods and compositions that facilitate such delivery and expression to tissues in vivo and in vitro. The disclosure further relates to replication competent retroviral vectors Retroviral Replicating Vectors (RRV) for these uses and in conjunction with methods and compositions that facilitate in vivo therapeutics.

BACKGROUND

Non-replicating viruses and viral vectors were originally proposed 20 years ago as anticancer agents using modalities that are ablative (e.g. prodrug activation such as thymidine kinase plus gancyclovir), restorative of normal cellular function (e.g., p53), immune activating (e.g., IL-2) or some combination of these (see, for example, Crofts and Krimsky Hum Gene Ther. 16:169-177, 2005). However, it has become apparent that non-replicative vectors are very inefficient in delivering genes to whole animals or patients as injection into tissues does not allow transduction past areas close to the needle track (see, e.g., Lang et al., J Clin Oncol 21:2508-2518, 2003) and injection into the vasculature or other body fluids makes the individual particles very susceptible to various arms of the immune system such as complement and pre-existing adaptive immunity (see, e.g., Liu et al., Hum Gene Ther. 20:621-629, 2009).

Therefore in the past few years there has been a revival of interest in the use of replicative viruses and replicative viral vectors as disease fighting agents in general, and anti-cancer agents in particular. With the advent of chemotherapy, radiation treatment and modern surgical techniques, enthusiasm for this approach lagged and for several decades these three approaches, along with the more recent addition of active immunotherapy with monoclonal antibodies, have been the major modes of treatment. However, the limitations of these four approaches on overall cancer mortality have become more and more apparent, and led first to the attempts at therapy with non-replicative viral vectors, and more recently, replicative vectors with and without additional genes. The hope has been that the viruses would replicate through tumors and destroy them directly or by expression of a transgene. Currently replicative viruses or viral vectors based on adenovirus, herpes virus, vesicular stomatitis virus, reovirus, vaccinia virus, measles virus, alpha virus and others are being investigated (Stanford et al., Cytokine Growth Factor Rev., 21:177-83, 2010).

Combination therapies are effective if dosing, side-effects and interactions are identified and modified appropriately for therapeutic benefit.

SUMMARY

The disclosure provides a method of treating a cancer, said method comprising administering to the cancer a replication competent mammalian oncoretroviral vector containing a therapeutic cassette, the therapeutic cassette comprising a gene encoding a polypeptide having prodrug-activating activity, wherein the vector infects the cancer cells and wherein the cancer cells expresses the gene encoding the polypeptide; and within about 5 days to about 12 weeks after administering the vector administering a prodrug and a cell cycle inhibiting drug. In another aspect, the disclosure provides a method of treating a cancer in a subject, comprising administering to the subject that is free of any chemotherapeutic agents a replication competent mammalian oncoretroviral vector containing a therapeutic cassette, the therapeutic cassette comprising a gene encoding a polypeptide having cytosine deaminase activity, allowing the vector to infect cancer cells of the cancer and spread, wherein the cancer cells expresses the gene encoding the polypeptide; and within about 5 to about 20 days after administering the vector administering 5-fluorocytosine and one or more chemotherapeutic agents such as temozolomide. In one embodiment, the one or more chemotherapeutic agents comprise a radio-sensitizing agent. In another embodiment of any of the foregoing, the cancer is glioblastoma multiforme. In a further embodiment, the glioblastoma multiforme is recurrent glioblastoma multiforme. In another embodiment, cell cycle inhibiting agent is temozolomide. In another embodiment, the temozolamide is administered in a plurality of 28-day cycles, each cycle comprising administration of a dose of about 50 to 150 mg/m$^2$ per day each day for at least days 1-5. In yet another embodiment, of any of the foregoing, prior to administration of the vector, the cancer is resected. In another embodiment, the method further comprises administering radiation to the subject at the cancer site within 1-5 days of administration of 5-FC and/or temozolomide. In yet another embodiment, the subject has not been treated with an agent that inhibits a mis-match repair process in the subject's cells. In another embodiment, the cancer is selected from the group consisting of lung cancer, colon-rectum cancer, breast cancer, prostate cancer, urinary tract cancer, uterine cancer, brain cancer, head and neck cancer, pancreatic cancer, melanoma, stomach cancer and ovarian cancer. In another embodiment, a replication competent retrovirus comprises: a retroviral GAG protein; a retroviral POL protein; a retroviral envelope; a retroviral polynucleotide comprising Long-Terminal Repeat (LTR) sequences at the 3' end of the retroviral polynucleotide sequence, a promoter sequence at the 5' end of the retroviral polynucleotide, said promoter being suitable for expression in a mammalian cell, a gag nucleic acid domain, a pol nucleic acid domain and an env nucleic acid domain; a therapeutic cassette comprising a regulatory domain operably linked to a heterologous gene encoding a polypeptide having cytosine deaminase activity, wherein the cassette is positioned 5' to the 3' LTR and 3' to the env nucleic acid domain encoding the retroviral envelope; and cis-acting sequences necessary for reverse transcription, packaging and integration in a target cell. In a further embodiment, the retroviral polynucleotide sequence is derived from murine leukemia virus (MLV), Moloney murine leukemia virus (MoMLV), Feline leukemia Virus or Gibbon ape leukemia virus (GALV). In yet a further embodiment, the MLV is an amphotropic MLV. In yet another embodiment, the retrovirus is a gammaretrovirus. In another embodiment of any of the foregoing, the polypeptide has cytosine deaminase activity and the prodrug is 5-fluorocytosine and the cell cycle inhibiting drug is temozolomide.

DETAILED DESCRIPTION

Figure 1:
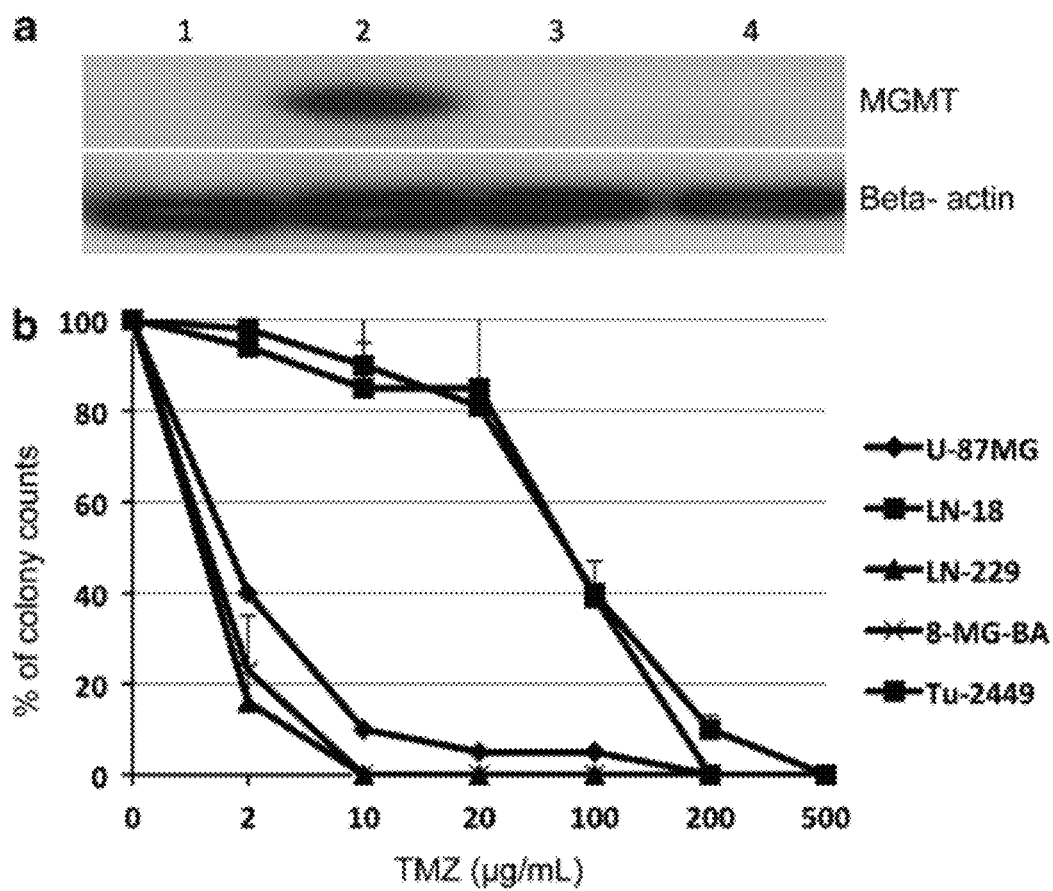
FIG. 1A-B shows assessment of temozolomide (TMZ) sensitivity in a panel of glioma cells. (A) The level of O-6-methylguanine-DNA methyltransferase (MGMT) protein expression was examined in four glioma cell lines (four human glioma) by western blot. Starting from the left, the cell lysates are as follows: (1) U-87MG; (2) LN-18; (3) LN-229 and (4) 8-MG-BA. b-Actin expression was used as a loading control. (B) Clonogenic assay was performed on the same four human tumor cell lines and a mouse glioma cell line, Tu-2449, with a range of TMZ concentrations to examine sensitivity.

As used herein and in the appended claims, the singular forms "a," "and," and "the" include plural referents unless the context clearly dictates otherwise. Thus, for example, reference to "an agent" includes a plurality of such agents and reference to "the cancer cell" includes reference to one or more cancer cells, and so forth.

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Any publications discussed above and throughout the text are provided solely for their disclosure prior to the filing date of the present application. Nothing herein is to be construed as an admission that the inventors are not entitled to antedate such disclosure by virtue of prior disclosure.

Patients with Newly Diagnosed High Grade Glioma are treated with standard of care procedures with some variation for individual patients. For example, the time frame between tumor resection and the start of chemoradiation is defined as 4 weeks but can range from approximately 1 to 12 weeks depending on circumstances. (see, e.g., (www).clinicaloptions.com/Oncology/Treatment%20Updates/GBM%20Satellite%202011/CCO%20Slidesets/Current_Treatment_Slides.aspx; R. Stupp et al., Clinical Practice Guidelines, Annals of Oncology 21 (Supplement 5): v190-v193, 2010).

Briefly, surgical resection is routinely performed in about 80% of newly diagnosed patients. Resection is contraindicated only where there is significant risk of damage to vital neurological structures, such as the speech center. In any case, the diagnoses of GBM is usually confirmed by a tumor biopsy and histopathological examination. Whether or not resection takes place, surgery or biopsy is followed by radiation and chemotherapy (TEMODAR®, temozolamide). In the case of resection there is usually a recovery period following surgery of 1-12 weeks before initiation of chemo-radiation. The first line standard chemo-radiation treatment is described in R. Stupp et al., N Engl J Med 2005; 352:987-96; Package insert for TEMODAR http://(www).accessdata.fda.gov/scripts/cder/drugsatfda/index.cfm?fuseaction=Search.Label_ApprovalHistory).

Combination treatments with complementary mechanisms of action can improve therapy of patients with cancers (e.g., glioblastoma). Early clinical investigations of systemic 5-FU as a single agent or in combination with radiation for the treatment of malignant glioma were not overly effective. However, recent studies suggest that the minimal response may have resulted from the limited availability of 5-FU in the tumor and not from the intrinsic resistance of gliomas to fluoropyrimidines. Pharmacokinetic studies show that 5-FU crosses the blood brain barrier, however, therapeutic concentrations may not be achieved in brain tissues at acceptable levels of toxicity to provide beneficial radioactive sensitization.

Toca 511 (vocimagene amiretrorepvec), a non-lytic, amphotropic retroviral replicating vector (RRV) (Tocagen Inc.) is a replication competent gamma-retrovirus derived from murine leukemia virus and contains an IRES cassette comprising a polynucleotide that encodes an enzyme having cytosine deaminase activity. Cytosine deaominase is a prodrug activating enzyme whose activity converts the orally available antifungal drug 5-fluorocytosine (5-FC) to the cytotoxic anticancer drug 5-FU in infected cancer cells. Toca 511 is currently in clinical trial for treating glioblastoma multiforme, but it and closely related RRV encoding prodrug activating genese have been shown to have effects on other cancer cells including diverse types such as colon cancer, bladder cancer, prostate cancer, breast cancer, lung cancer, and mesothelioma (C. Dalba et al Current Gene Ther. 5:655-667 2005; K. Hiraoka et al. Cancer Res. 67:5345-5354 2007; E. Kikuchi Clin Cancer Res 13:4511-4518 2007; Y. Kawasaki et al. Cancer Gene Therapy 18: 571-578 2011). Toca 511 is delivered to dividing cells such as cancer cells where it integrates and produces additional viral particles, which in turn infect neighboring cells increasing the viral load in the cancer tissue. Toca 511 has been shown to have multiple integrations in the host cell genome thereby increasing the amount of the gene encoding the polypeptide that converts a prodrug to a cytotoxic drug in the infected cells. To obtain high levels of cytotoxic gene expression in the infected tissue, the replication competent vector needs to spread and infect neighboring tissue. RRVs are designed to utilize the host cell machinery to carry out this process effectively. In some instances, however, both external and/or internal agents (a) decrease the ability of the infected cell to replicate or transcribe DNA, or (b) increase the cells ability to clear infectious particles.

Toca 511 selectively infects and replicates in the tumor environment. Toca 511 can then spread through the tumor when infected tumor cells produce infectious virus that buds off from the infected cell and spreads to neighboring replicating tumor cells. Infected cells and their daughter cells then constitutively express a polypeptide having cytosine deaminase activity (CD), rendering them capable of enzymatic conversion of the orally available prodrug 5-FC into the potent anticancer drug 5-fluorouracil (5-FU).

Cytosine deaminase (EC 3.5.4.1) is an enzyme that catalyzes the chemical reaction $$\text{cytosine} + H_2 \rightarrow \text{uracil} + NH_3$$

Thus, the two substrates of this enzyme are cytosine and $H_2O$, whereas its two products are uracil and $NH_3$. This enzyme belongs to the family of hydrolases, those acting on carbon-nitrogen bonds other than peptide bonds, specifically in cyclic amidines. The systematic name of this enzyme class is cytosine aminohydrolase. This enzyme is also called isocytosine deaminase. This enzyme participates in pyrimidine metabolism.

More particularly, cytosine deaminase is an enzyme involved in the metabolic pathway for pyrimidines, through which exogenous cytosine is transformed, via hydrolytic deamination, into uracil. Cytosine deaminase (CDase or CD) activities have been demonstrated in prokaryotes and lower eukaryotes, but they are absent in mammals (Koechlin et al., 1966, Biochem. Pharmacol. 15, 435-446; Polak et al., 1976, Chemotherapy 22, 137-153). The FCY1 gene of *Saccharomyces cerevisiae* (*S. cerevisiae*) and the coda gene of *E. coli*, which encode, respectively, the CDase of these two organisms, are known and their sequences are published (EP 402 108; Erbs et al., 1997, Curr. Genet. 31, 1-6; WO 93/01281). CDase also deaminates a cytosine analogue, 5-fluorocytosine (5-FC) to 5-fluorouracil (5-FU), which is a highly cytotoxic compound, in particular when it is converted to 5-fluoro-UMP (5-FUMP) or 5-fluoro-dUMP (F-dUMP). Cells which lack CDase activity, due either to an inactivating mutation of the gene encoding the enzyme or to their natural deficiency for this enzyme (for example mammalian cells) are resistant to 5-FC (Jund and Lacroute, 1970, J. Bacteriol. 102, 607-615; Kilstrup et al., 1989, J. Bacteriol., 171, 2124-2127). On the other hand, it has been demonstrated that it is possible to transmit 5-FC sensitivity to mammalian cells into which the sequence encoding a CDase activity has been transferred (Huber et al., 1993, Cancer Res. 53, 4619-4626; Mullen et al., 1992, Proc. Natl. Acad. Sci. USA 89, 33-37; WO 93/01281). Accordingly, the use of CD is advantageous in the context of gene therapy, in particular anticancer gene therapy.

Anabolites of 5-FU alter DNA and RNA synthesis, leading to cell cycle arrest and apoptosis. Through a process called metabolic cooperation, 5-FU can diffuse from infected cells and induce cell death in nearby replicating cells but spares nonreplicating tissue, which is resistant to 5-FU killing. This local Toca 511+5-FC-mediated production of 5-FU avoids systemic exposure to high levels of 5-FU, especially given the very short half-life of 5-FU because of its rapid degradation by the ubiquitous catabolic enzyme dihydropyrimidine dehydrogenase. Currently, Toca 511-mediated gene transfer followed by cyclic courses of oral 5-FC (in humans, Toca FC, an extended release formulation, see, e.g., WO201002937, which is incorporated herein by reference) is under investigation in two Phase 1 ascending dose clinical trials in patients with recurrent high-grade glioma that has progressed after treatment with surgery, radiation and TMZ.

5-Fluorouracil (5-FU) is one of the most commonly used chemotherapeutic agents for certain cancers and has been used extensively with radiation. There are a number of mechanisms by which 5-FU could increase radiation sensitivity at the cellular level. One mechanism is thought to be through the killing of S-phase cells, which are relatively radioresistant. Radiosensitization under non-cytotoxic conditions occurs only when cells are incubated with the drug before and during radiation. Thus, several studies have suggested that 5-FU should be given continuously during a course of fractionated radiation to achieve radiosensitization of most fractions. Indeed, the use of protracted venous infusion of 5-FU has become a standard therapy for rectal cancer (Rich et al., Oncology 13: 131-134, 1999). However, protracted venous infusion over a 5- to 6-week period is relatively complex, requiring specialized pumps and long-term venous access which makes the patients susceptible to infection.

Temozolomide (TMZ), an oral alkylating agent, is the standard chemotherapy treatment for patients with newly diagnosed glioblastoma multiforme (GBM), the most common and aggressive form of primary brain cancer in adults. An induction dose of TMZ at 75 mg $m^{-2}$ is used with concurrent radiation after resection for these patients followed by a maintenance dose of 150-200 mg $m^{-2}$. However, tumors that express the enzymes O-6-methylguanine-DNA methyltransferase (MGMT) or O-6-alkylguanine-DNA alkyltransferase are relatively resistant to this treatment because of the enzymes' ability to repair the TMZ-induced methylation damage to the tumor DNA. Tumors with hypermethylated MGMT promoters have reduced gene expression and make less repair protein. Nevertheless, both MGMT hypermethylated and unmethylated tumors almost inevitably recur and overall 5-year survival remains at <5%. The median overall survival for newly diagnosed GBM patients remains at <12 months, whereas the landmark Stupp study showed that for those receiving TMZ and radiation in addition to resection, it is approximately 14.6 months. When the MGMT promoter is methylated, the median survival is 21.7 months. It is clear that additional combinatorial approaches are necessary to significantly improve patient outcomes. Of particular interest are combinations of TMZ with agents that have complementary mechanisms of action, and strategies that minimize toxicity.

Synergistic effects of 5-FU and TMZ have been demonstrated. DNA damage Induced by anabolites of 5-FU through incorporation of 5-FdUTP into DNA and reduction of thymidine pools by inhibition of thymidylate synthase via 5-FdUMP reduces the repair activity of MGMT, thereby potentiating the effects of TMZ on DNA replication. For example, capecitabine (5-DFUR), an oral pro-drug for 5-FU, and TMZ were synergistic for induction of apoptosis in human NET cell lines. In addition, secondary effects related to sensitization by yet other cancer treatments can potentiate treatment. For example, both 5-FU and TMZ have been demonstrated to be radiation sensitizer.

A radiation sensitizer is an agent used to enhance the effect of radiation therapy. In delivering potentially curative doses of radiation, it is necessary to balance the need for local tumor control with the potential for damage to surrounding normal tissues by the delivered dose of radiation (Bush et al., 1978). It is therefore desirable to use the lowest radiation dose consistent with local control. One way to achieve this would be to utilize a radiation sensitizing agent to enhance cytotoxicity of delivered radiation to the tumor, thus allowing lower radiation doses while maintaining tumor killing.

Radiation causes cell death by damaging critical targets within the cell, most commonly chromosomal DNA (Hendrickson and Withers, 1991). Radiation therapy relies on two types of ionizing radiation: (1) directly ionizing subatomic particle radiation, such as alpha particles and beta particles (electrons), neutrons, protons, mesons, heavy charged ions, etc., and (2) indirectly ionizing electromagnetic radiation, which exists as a family of waves of varying frequency including high frequency x-rays or gamma rays. However, of the two, electromagnetic radiation is more commonly used in radiation therapy today. In tissue, electromagnetic radiation in the form of x-rays or gamma rays can interact with molecules (especially water) causing the ejection of high-energy electrons. The electrons can break the sugar phosphate bonds in DNA directly (direct action) or the process of electron ejection can ultimately produce free (uncharged) radicals that can also break the chemical (sugar-phosphate) bonds in DNA (indirect action). The damage caused through the indirect mechanism is more significant (Hendrickson and Withers, 1991; Mulcahy et al., 1993; Rubin and Siemann, 1993; Chapman et al., 1974).

Radiation damage is produced primarily by hydroxyl radicals. This radical is extremely reactive and short lived. It causes damage primarily in the vicinity in which it is generated (~4 nm). If it comes into contact with a hydrated electron it is deactivated by conversion to a hydroxide ion. Hydrated electrons are strong reducing species and highly energetic. They are very mobile by comparison to the hydroxyl radical, can travel distances quickly, and through direct action can damage DNA. However, as mentioned above, they also deactivate hydroxyl radicals readily. Agents with strong electron affinity, by virtue of "soaking up" solvated electrons, prevent them from neutralizing hydroxyl radicals and thereby allow hydroxyl radicals to exert their effect (Adams and Dewey, 1963). Oxygen and other compounds with strong electron affinity would thus be expected to act as radiation sensitizers.

Typically, Toca 511 or other therapeutic vectors are administered into the GBM resection cavity at the time of resection or into the non-resected tumor at doses up to $3 \times 10^7$ TU/gm brain (e.g., about $5 \times 10^{10}$ total TU) per administration, and the therapeutic RRV allowed to spread for 1 to 12 weeks before the start of chemo-radiation and prodrug administration. In the case of Toca 511 (T5.0002), the prodrug is 5-FC. 5-FC is converted to 5-FU in the tumor by the vector encoded polypeptide having cytosine deaminase activity. This procedure and resultant 5-FU is shown wherein to be synergistic with temozolomide; 5-FU is also known to be synergistic with radiation for ablative tumor therapy.

Thus the disclosure describes methods and composition useful to improve cancer treatment by overcoming many of the difficulties associated with single therapeutic regimens, by provided radio-sensitized cancer cells using local 5-FU sensitizing. The disclosure also provides methods of improving radiations therapy in a subject having cancer. The method includes adjuvant therapy with radiation following delivery of a retroviral vector of the disclosure expressing a cytosine deaminase that converts the inactive prodrug 5-fluorcytosine (5-FC) to the cytotoxic drug 5-fluorouracil (5-FU). The disclosure also demonstrates that a combination of 5-FC with TMZ act synergistically in cancers to improve cell killing.

5-FU is a known radiosensitizing agent, and also synergizes with TMZ given its distinct mechanism of action. However, prior to the present disclosure the effect of TMZ on RRV therapy with CD was unknown. For example, TMZ inhibition of replication could interfere with the initial infection and spread of the RRV. TMZ co-administered with 5-FC could impact the production of and effect of 5-FU-mediated tumor cell death. The combination of TMZ and 5-FC or 5-FU could result in unacceptable systemic toxicity. The disclosure provide combination therapy that examines TMZ in combination with Toca 511 and 5-FC in TMZ-sensitive and -resistant glioma cell lines both in vitro and in vivo in mice for efficacy and toxicity. The disclosure demonstrates that TMZ does not interfere with Toca 511+5-FC-mediated cell killing in the glioma tumor cells, regardless of their sensitivity to TMZ in vitro, and that there were no significant hematologic effects from 5-FC-TMZ combination treatments in vivo. Furthermore, mice with a glioma from a TMZ-resistant glioma cell line survive equally well with and without TMZ administration when treated with Toca 511 and 5-FC so long as the TMZ is administered after Toca 511 and its initial time for spread. In addition, the disclosure demonstrates that a synergistic long-term survival advantage is observed when TMZ, in combination with Toca 511+5-FC treatment, was administered to mice bearing an orthotopic TMZ-sensitive glioma tumor. These results provide support for the use of this combination treatment strategy for newly diagnosed patients with primary GBM.

In addition, as mentioned above, a combination therapy for the treatment of cancers which includes an RRV (e.g., Toca 511) should be planned and performed based upon the effect a primary chemotherapeutic agent has on cell cycle and viral spread. Furthermore, agents that act as radiation sensitizing agents can be administered with 5-FC to patients treated with Toca 511 to improve radiation treatment. Accordingly, administration of RRV can be optimized with consideration of treatments with cell cycle inhibitors.

"Cell Cycle Inhibitor" as used herein refers to any protein, peptide, chemical or other molecule which delays or impairs a dividing cell's ability to progress through the cell cycle and replicate. Cell cycle inhibitors which prolong or arrest mitosis (M-phase) or DNA synthesis (S-phase) can increase the dividing cell's sensitivity to the effects of radiation, however, their effect on RRV infection should be determined. A wide variety of methods may be utilized to determine the ability of a compound to inhibit the cell cycle including univariate analysis of cellular DNA content and multiparameter analysis. Similarly, the effect of cell cycle inhibitors to affect RRV infection and spread can be determined as described below. A Cell Cycle Inhibitor may act to inhibit the cell cycle at any of the steps of the biological pathways, as well as at other possible steps in other biological pathways. In addition, it should be understood that while a single cell cycle agent is often referred to, that this in fact should be understood to include two or more cell cycle agents, as more than one cell cycle agent may be utilized within the compositions, methods and/or devices described herein.

A wide variety of cell cycle inhibitory agents are known, either with or without a carrier (e.g., a polymer or ointment or vector), in order to treat or prevent a hyperproliferative disease. Representative examples of such agents include taxanes (e.g., paclitaxel and docetaxel) (Schiff et al., Nature 277:665-667, 1979; Long and Fairchild, Cancer Research 54:4355-4361, 1994; Ringel and Horwitz, J. Nat'l Cancer Inst. 83(4):288-291, 1991; Pazdur et al., Cancer Treat. Rev. 19(40): 351-386, 1993), Etanidazole, Nimorazole (B. A. Chabner and D. L. Longo. Cancer Chemotherapy and Biotherapy—Principles and Practice. Lippincott-Raven Publishers, New York, 1996, p. 554), perfluorochemicals with hyperbaric oxygen, transfusion, erythropoietin, BW12C, nicotinamide, hydralazine, BSO, WR-2721, IudR, DUdR, WR-2721, BSO, mono-substituted keto-aldehyde compounds (L. G. Egyud. Keto-aldehyde-amine addition products and method of making same. U.S. Pat. No. 4,066,650, Jan. 3, 1978), nitroimidazole (K. C. Agrawal and M. Sakaguchi. Nitroimidazole radiosensitizers for Hypoxic tumor cells and compositions thereof. U.S. Pat. No. 4,462,992, Jul. 31, 1984), 5-substituted-4-nitroimidazoles (Adams et al., Int. J. Radiat. Biol. Relat. Stud. Phys., Chem. Med. 40(2): 153-61, 1981), SR-2508 (Brown et al., Int. J. Radiat. Oncol. Biol. Phys. 7(6):695-703, 1981), 2H-isoindolediones (J. A. Myers, 2H-Isoindolediones, their synthesis and use as radiosensitizers. U.S. Pat. No. 4,494,547, Jan. 22, 1985), chiral [[(2-bromoethyl)-amino]methyl]-nitro-1H-imidazole-1-ethanol (V. G. Beylin, et al., Process for preparing chiral [((2-bromoethyl)-amino)methy-1]-nitro-1H-imidazole-1-ethanol and related compounds. U.S. Pat. No. 5,543,527, Aug. 6, 1996; U.S. Pat. No. 4,797,397; Jan. 10, 1989; U.S. Pat. No. 5,342,959, Aug. 30, 1994), nitroaniline derivatives (W. A. Denny, et al Nitroaniline derivatives and their use as anti-tumor agents. U.S. Pat. No. 5,571,845, Nov. 5, 1996), DNA-affinic hypoxia selective cytotoxins (M. V. Papadopoulou-Rosenzweig. DNA-affinic hypoxia selective cytotoxins. U.S. Pat. No. 5,602,142, Feb. 11, 1997), halogenated DNA ligand (R. F. Martin. Halogenated DNA ligand radiosensitizers for cancer therapy. U.S. Pat. No. 5,641,764, Jun. 24, 1997), 1,2,4 benzotriazine oxides (W. W. Lee et al. 1,2,4-benzotriazine oxides as radiosensitizers and selective cytotoxic agents. U.S. Pat. No. 5,616,584, Apr. 1, 1997; U.S. Pat. No. 5,624,925, Apr. 29, 1997; Process for Preparing 1,2,4 Benzotriazine oxides. U.S. Pat. No. 5,175,287, Dec. 29, 1992), nitric oxide (J. B. Mitchell et al., Use of Nitric oxide releasing compounds as hypoxic cell radiation sensitizers. U.S. Pat. No. 5,650,442, Jul. 22, 1997), 2-nitroimidazole derivatives (M. J. Suto et al. 2-Nitroimidazole derivatives useful as radiosensitizers for hypoxic tumor cells. U.S. Pat. No. 4,797,397, Jan. 10, 1989; T. Suzuki. 2-Nitroimidazole derivative, production thereof, and radiosensitizer containing the same as active ingredient. U.S. Pat. No. 5,270,330, Dec. 14, 1993; T. Suzuki et al. 2-Nitroimidazole derivative, production thereof, and radiosensitizer containing the same as active ingredient. U.S. Pat. No. 5,270,330, Dec. 14, 1993; T. Suzuki. 2-Nitroimidazole derivative, production thereof and radiosensitizer containing the same as active ingredient; Patent EP 0 513 351 B1, Jan. 24, 1991), fluorine-containing nitroazole derivatives (T. Kagiya. Fluorine-containing nitroazole derivatives and radiosensitizer comprising the same. U.S. Pat. No. 4,927,941, May 22, 1990), copper (M. J. Abrams. Copper Radiosensitizers. U.S. Pat. No. 5,100,885, Mar. 31, 1992), combination modality cancer therapy (D. H. Picker et al. Combination modality cancer therapy. U.S. Pat. No. 4,681,091, Jul. 21, 1987). 5-CldC or (d) $H_4U$ or 5-halo-2'-halo-2'-deoxy-cytidine or -uridine derivatives (S. B. Greer. Method and Materials for sensitizing neoplastic tissue to radiation. U.S. Pat. No. 4,894,364 Jan. 16, 1990), platinum complexes (K. A. Skov. Platinum Complexes with one radiosensitizing ligand. U.S. Pat. No. 4,921,963. May 1, 1990; K. A. Skov. Platinum Complexes with one radiosensitizing ligand. Patent EP 0 287 317 A3), fluorine-containing nitroazole (T. Kagiya, et al. Fluorine-containing nitroazole derivatives and radiosensitizer comprising the same. U.S. Pat. No. 4,927,941. May 22, 1990), benzamide (W. W. Lee. Substituted Benzamide Radiosensitizers. U.S. Pat. No. 5,032,617, Jul. 16, 1991), autobiotics (L. G. Egyud. Autobiotics and their use in eliminating nonself cells in vivo. U.S. Pat. No. 5,147,652. Sep. 15, 1992), benzamide and nicotinamide (W. W. Lee et al Benzamide and Nictoinamide Radiosensitizers. U.S. Pat. No. 5,215,738, Jun. 1, 1993), acridine-intercalator (M. Papadopoulou-Rosenzweig. Acridine Intercalator based hypoxia selective cytotoxins. U.S. Pat. No. 5,294,715, Mar. 15, 1994), fluorine-containing nitroimidazole (T. Kagiya et al. Fluorine containing nitroimidazole compounds. U.S. Pat. No. 5,304,654, Apr. 19, 1994), hydroxylated texaphyrins (J. L. Sessler et al. Hydroxylated texaphrins. U.S. Pat. No. 5,457,183, Oct. 10, 1995), hydroxylated compound derivative (T. Suzuki et al. Heterocyclic compound derivative, production thereof and radiosensitizer and antiviral agent containing said derivative as active ingredient. Publication Number 011106775 A (Japan), Oct. 22, 1987; T. Suzuki et al. Heterocyclic compound derivative, production thereof and radiosensitizer, antiviral agent and anti cancer agent containing said derivative as active ingredient. Publication Number 01139596 A (Japan), Nov. 25, 1987; S. Sakaguchi et al. Heterocyclic compound derivative, its production and radiosensitizer containing said derivative as active ingredient; Publication Number 63170375 A (Japan), Jan. 7, 1987), fluorine containing 3-nitro-1,2,4-triazole (T. Kagitani et al. Novel fluorine-containing 3-nitro-1,2,4-triazole and radiosensitizer containing same compound. Publication Number 02076861 A (Japan), Mar. 31, 1988), 5-thiotretrazole derivative or its salt (E. Kano et al Radiosensitizer for Hypoxic cell. Publication Number 61010511 A (Japan), Jun. 26, 1984), Nitrothiazole (T Kagitani et al. Radiation-sensitizing agent. Publication Number 61167616 A (Japan) Jan. 22, 1985), imidazole derivatives (S. Inayma et al. Imidazole derivative. Publication Number 6203767 A (Japan) Aug. 1, 1985; Publication Number 62030768 A (Japan) Aug. 1, 1985; Publication Number 62030777 A (Japan) Aug. 1, 1985), 4-nitro-1,2,3-triazole (T. Kagitani et al., Radiosensitizer. Publication Number 62039525 A (Japan), Aug. 15, 1985), 3-nitro-1,2,4-triazole (T. Kagitani et al Radiosensitizer. Publication Number 62138427 A (Japan), Dec. 12, 1985), Carcinostatic action regulator (H. Amagase. Carcinostatic action regulator. Publication Number 63099017 A (Japan), Nov. 21, 1986), 4,5-dinitroimidazole derivative (S. Inayama. 4,5-Dinitroimidazole derivative. Publication Number 63310873 A (Japan) Jun. 9, 1987), nitrotriazole Compound (T. Kagitanil. Nitrotriazole Compound. Publication Number 07149737 A (Japan) Jun. 22, 1993), cisplatin, doxorubin, misonidazole, mitomycin, tiripazamine, nitrosourea, mercaptopurine, methotrexate, flurouracil, bleomycin, vincristine, carboplatin, epirubicin, doxorubicin, cyclophosphamide, vindesine, etoposide (I. F. Tannock. Review Article: Treatment of Cancer with Radiation and Drugs. Journal of Clinical Oncology 14(12):3156-3174, 1996), camptothecin (Ewend M. G. et al. Local delivery of chemotherapy and concurrent external beam radiotherapy prolongs survival in metastatic brain tumor models. (Cancer Research 56(22):5217-5223, 1996; Tishler R. B. et al. Taxol:

a novel radiation sensitizer. International Journal of Radiation Oncology and Biological Physics 22(3):613-617, 1992).

A number of the above-mentioned cell cycle inhibitors also have a wide variety of analogues and derivatives known to those of skill in the art, including, but not limited to, cisplatin, cyclophosphamide, misonidazole, tiripazamine, nitrosourea, mercaptopurine, methotrexate, flurouracil, epirubicin, doxorubicin, vindesine and etoposide.

Accordingly, in one embodiment, the disclosure provides a method of treating a cancer comprising administering to a subject having a cancer an RRV comprising a gene that catalyzes the conversion of a prodrug to a cytotoxic drug. In one embodiment, the gene encodes a polypeptide having cytosine deaminase activity. In another embodiment, the RRV comprises a replication competent mammalian oncovirus that comprises an IRES cassette just downstream (e.g., within 1 to 80 bp) of the termination codon for the envelop gene and upstream of the 3'LTR. In another embodiment, the RRV comprises a therapeutic cassette that comprises a regulatory domain (e.g., an IRES, small promoter, mini-promoter or a combination of at least two of the foregoing) linked to a gene or nucleic acid sequence to be delivered to a cell. Examples of RRV's that can be used in the methods of the disclosure can be found in U.S. Pat. Publication Nos. 2011-0217267-A1 and 2011-0287020-A1 (see, e.g., SEQ ID NOs: 19-22), and International Application No. PCT/US2013/066709, the disclosure of which are incorporated herein by reference. The RRV is allowed to spread and infect the cancer tissue. In one embodiment, the RRV is administered about 1-4 weeks following any prior chemotherapeutic treatment (e.g., 1-4 week washout prior to delivery of an RRV). In another embodiment the RRV is allowed to spread and replicate in the cancer tissue for about 5 days to about 12 weeks (e.g., 5-10 days, 10-12 days, 12-15 days, 15-20 days, 20-40 days, 40-60 days, 60-90 days) prior to delivery of any chemotherapeutic agent. In one embodiment, the subject is not currently having a therapy with an agent that effects mis-match repair within the cell. In one embodiment, the subject has not been treated with an agent that inhibits the mis-match repair (MMR) process of the cell. In another embodiment, if the subject has been treated with an inhibitor of MMR, the subject undergoes a washout period prior to administration of an RRV.

Figure 6:
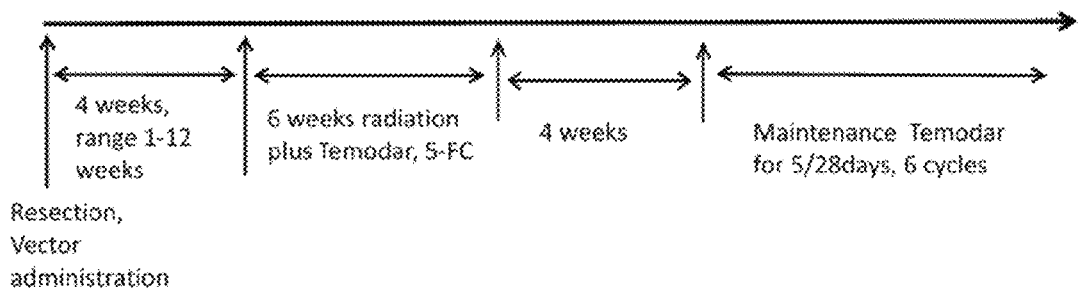
FIG. 6 shows a treatment cycle of the disclosure.

Administration of the RRV into a resection cavity is typically by multiple injections spaced throughout the cavity, by coating the interior of the cavity with vector mixed with an application gel such as one made from gelatin (e.g. Surgifoam®), by injection through a sheet of hemostasis agent such as Surgifoam or by a combination of these methods. The RRV can also be administered IV or into other blood vessels by using higher doses of RRV (up to $10^9$ TU/ml blood), or by further combinations with the previous injection and gel methods. A simple schema for the treatment protocol for administration into the resectin cavity is shown in FIG. 6, but other schedules that allow RRV spread in the absence of TEMODAR then exploit the synergy of 5-FC/cytosine deaminase with temozolomide are possible. For example, administration of vector after the initial temozolomide and radiation treatment also allows approximately 4 weeks for vector spread. The 5-FC can be administered 1 week out of 2, one week out of 3 or one week out of 4 at doses between 50 and 200 mg/kg/day. Other well tolerated dosing schemes will be obvious to one skilled in the art.

In use, the retroviral vector(s) will replicate through the tumor or other target tissue and before growth inhibition occurs the virus first integrates into the host genome and continues to make virus after growth of that cell is inhibited.

Once the RRV is sufficiently established in the cancer cell, the subject can be administered a prodrug, prior to, simultaneously with or immediately after administration of a chemotherapeutic agent. In one embodiment, the chemotherapeutic agent is a radiosensitizing agent. In another embodiment, the agent is temozolomide (TMZ).

Temozolomide is typically administered at about 75 mg/m$^2$ daily for 42 days concomitant with focal radiotherapy (60 Gy administered in 30 fractions -2 Gy/day for 5 days a week over 6 weeks) followed by a four week rest then maintenance temozolomide for 6 cycles. Focal radiation therapy during TMZ therapy typically includes the tumor bed or resection site with a 2- to 3-cm margin; no dose reductions are recommended during the concomitant phase; however, dose interruptions or discontinuation may occur based on toxicity. Typically, the temozolomide dose should be continued throughout the 42-day concomitant period up to 49 days if all of the following conditions are met: absolute neutrophil count greater than or equal to $1.5 \times 10^9$/L, platelet count greater than or equal to $100 \times 10^9$/L, common toxicity criteria (CTC) non-hematological toxicity less than or equal to Grade 1 (except for alopecia, nausea, and vomiting). During treatment a complete blood count should be obtained weekly. Temozolomide dosing should be interrupted or discontinued during concomitant phase according to the hematological and non-hematological toxicity criteria as noted in the FDA TEMODAR package insert at Table 1. *Pneumocystis carinii* pneumonia (PCP) prophylaxis is required during the concomitant administration of temozolomide and radiotherapy, and should be continued in patients who develop lymphocytopenia until recovery from lymphocytopenia (CTC Grade less than or equal to 1).

The maintenance phase of temozolomide includes a plurality of cycles. For example, Cycle 1: Four weeks after completing the temozolomide and radiation therapy phase, temozolomide is administered for an additional 6 cycles of maintenance treatment with temozolomide dosed for cycles of 5 consecutive days followed by 23 days off. Dosage in Cycle 1 (maintenance) is 150 mg/m$^2$ once daily for 5 days followed by 23 days without treatment. Cycles 2-6: At the start of Cycle 2, the dose can be escalated to 200 mg/m$^2$, if the CTC nonhematologic toxicity for Cycle 1 is Grade less than or equal to 2 (except for alopecia, nausea, and vomiting), absolute neutrophil count (ANC) is greater than or equal to $1.5 \times 10^9$/L, and the platelet count is greater than or equal to $100 \times 10^9$/L. The dose remains at 200 mg/m$^2$ per day for the first 5 days of each subsequent cycle except if toxicity occurs. If the dose was not escalated at Cycle 2, escalation should not be done in subsequent cycles.

Temozolomide is adjusted according to nadir neutrophil and platelet counts in the various cycles. For temozolomide dosage calculations based on body surface area (BSA), see Table 5 of the package insert.

The disclosure provides a method of treating glioblastoma multiforme, the method comprising administering to said tumor bed tissue a replication competent retroviral vector (RRV) comprising a gene encoding a polypeptide having cytosine deaminase activity, wherein the RRV transfects the tumor bed tissue and the tumor bed tissue expresses the gene encoding the polypeptide having cytosine deaminase. Subsequently (e.g., within about 5 days to about 12 weeks after administering said RRV, further administering 5-fluorocytosine and temozolomide. In one embodiment, the glioblastoma multiforme is recurrent glioblastoma multiforme. In another embodiment, the temozolamide is administered in a plurality of 28-day cycles, each cycle comprising administration of a dose of about 75 to 150 mg/m$^2$ per day each day for days 1-5 of said 28-day cycle, followed by a dose of about 0 to 150 mg/m² per day for days 6-28 of said 28-day cycle. In another embodiment, the subject is administered 5-fluorocytosine prior to, simultaneously with, or immediately following administration of TMZ. In another embodiment, the subject is treated with radiation therapy within 24 hours of administration of TMZ and 5-fluorocytosine. In another embodiment, administering of temozolomide is begun within not more than about seven days after beginning to administer 5-fluorocytosine. In one embodiment, the administration of temozolomide is begun about the same time as administering of 5-fluorocytosine.

The disclosure also demonstrates that retroviral treatment with a recombinant polynucleotide encoding a polypeptide with cytosine deaminase activity followed by 5-FC therapy and temozolomide improves radiation sensitization of the infected cancer cells. As mentioned above, temozolomide is an effective radiation sensitizing agent. Other radiation sensitizing agents can be used in combination with 5-FC administration or 5-FC and temozolomide administration.

The disclosure provides a method of treating a subject having a cell proliferative disorder. The subject can be any mammal, and is preferably a human. The subject is contacted with a recombinant replication competent retroviral vector of the disclosure. The contacting can be in vivo or ex vivo. Methods of administering the retroviral vector of the disclosure are known in the art and include, for example, systemic administration, topical administration, intraperitoneal administration, intra-muscular administration, intracranial, cerebrospinal, as well as administration directly at the site of a tumor or cell-proliferative disorder, and other routes of administration known in the art.

For example, the disclosure provides methods for treating cell proliferative disorders such as cancer and neoplasms comprising administering an RRV of the disclosure followed by treatment with a chemotherapeutic agent or anti-cancer agent. In one aspect, the RRV is administered to a subject for a period of time prior to administration of the chemotherapeutic or anti-cancer agent that allows the RRV to infect and replicate. The vector may be administered locally (e.g., at the site of the tumor) or may be systemically administered (e.g., intravenously into the circulation). Advantageously the vector is capable of crossing the blood brain barrier and transduces/infects tumor cells of the brain. Doses of the vector may be given daily by single dose or multiple doses and may be give periodically during the treatment (e.g., every day for several days, every other day for several days and the like). The data demonstrate that the doses IV may be given once with sufficient transduction/infection in brain cancer cells. Typically the dose will be about $9 \times 10^6$ TU/100 µl; however, the dose may range from about $10^5$ to about $10^{12}$ TU given in one or more doses of 100 µl or scaled appropriately by blood value for larger animals and humans (roughly 2500 fold for a human compared to a mouse).

Any number of the foregoing embodiments (e.g., vector constructs, heterologous genes etc.) can be used in combination with steroid, steroid antagonists, radiation, anti-IFN, IFN, and the like. As demonstrated herein, various combination therapies comprising (i) radiation treatment following viral therapy with a vector expressing a cytosine deaminase and under going 5-FC therapy can be used, (ii) anti-IFN or other therapies to reduce innate antiviral activity can be used in combination with any of the foregoing vectors, (iii) steroids can be used in combination with any of the vectors of the disclosure to promote viral infection and spread (iv) anti-progestins such as mifepristone can be used in combination with any of the vectors of the disclosure to promote viral infection and spread. These and other embodiments are further described elsewhere herein. One of skill in the art can monitor the therapeutic activity of a polypeptide having cytosine deaminase activity in any of the foregoing combination therapies or in any of the vectors described above comprising a polynucleotide that expresses a polypeptide having cytosine deaminase activity; the method comprising measuring FBAL in a sample from the subject.

Thus, the disclosure includes various pharmaceutical compositions useful for treating a cell proliferative disorder. The pharmaceutical compositions according to the disclosure are prepared by bringing a retroviral vector containing a heterologous polynucleotide sequence useful in treating or modulating a cell proliferative disorder according to the disclosure into a form suitable for administration to a subject using carriers, excipients and additives or auxiliaries. In some embodiments, the retroviral vector is formulated in combination with a PPR or IFN pathway inhibitor. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol and polyhydric alcohols, hemostatic agents such as absorbable gelatin, with or without thrombin. Intravenous vehicles include fluid and nutrient replenishers. Preservatives include antimicrobial, anti-oxidants, chelating agents and inert gases. Other pharmaceutically acceptable carriers include aqueous solutions, non-toxic excipients, including salts, preservatives, buffers and the like, as described, for instance, in Remington's Pharmaceutical Sciences, 15th ed. Easton: Mack Publishing Co., 1405-1412, 1461-1487 (1975) and The National Formulary XIV., 14th ed. Washington: American Pharmaceutical Association (1975), the contents of which are hereby incorporated by reference. The pH and exact concentration of the various components of the pharmaceutical composition are adjusted according to routine skills in the art. See Goodman and Gilman's The Pharmacological Basis for Therapeutics (7th ed.).

In some embodiments of the disclosure a therapy comprises replication competent viral vectors that contain a heterologous polynucleotide encoding, for example, a cytosine deaminase or mutant thereof, an miRNA or siRNA, a cytokine, an antibody binding domain, or the like, or combinations thereof, that can be delivered to a cell or subject. The viral vector can be an adenoviral vector, a measles vector, a herpes vector, a retroviral vector (including a lentiviral vector), a rhabdoviral vector such as a Vesicular Stomatitis viral vector, a reovirus vector, a Seneca Valley Virus vector, a poxvirus vector (including animal pox or vaccinia derived vectors), a parvovirus vector (including an AAV vector), an alphavirus vector or other viral vector known to one skilled in the art (see also, e.g., *Concepts in Genetic Medicine*, ed. Boro Dropulic and Barrie Carter, Wiley, 2008, Hoboken, N.J.; *The Development of Human Gene Therapy*, ed. Theodore Friedmann, Cold Springs Harbor Laboratory Press, Cold springs Harbor, N.Y., 1999; *Gene and Cell Therapy*, ed. Nancy Smyth Templeton, Marcel Dekker Inc., New York, N.Y., 2000 and *Gene Therapy: Therapeutic Mechanism and Strategies*, ed. Nancy Smyth Templetone and Danilo D Lasic, Marcel Dekker, Inc., New York, N.Y., 2000; the disclosures of which are incorporated herein by reference).

In certain embodiments, the viral vector is a replication competent retroviral vector (RRV) capable of infecting only replicating mammalian cells. In another embodiment, a replication competent retroviral vector used in the compositions and methods of the disclosure comprises a regulatory domain (e.g., an internal ribosomal entry site (IRES), mini-promoter, core promoter or any combination thereof) 5' to a heterologous polynucleotide encoding, e.g., a cytosine deaminase, miRNA, siRNA, cytokine, receptor, antibody or the like. When the heterologous polynucleotide encodes a non-translated RNA such as siRNA, miRNA or RNAi then an IRES is typically not used, but rather a polIII promoter is used; however, the IRES may be included where another hetereologous polynucleotide may be desirably expressed. In one embodiment, the siRNA, miRNA, RNAi polynucleotide is 3' to an ENV polynucleotide of a retroviral vector. In another embodiment the siRNA, miRNA, RNAi polynucleotide is expressed from a pol III promoter such as trhe H1 promoter. In yet another embodiment, an IRES cassette comprising an internal ribosome entry site operably linked to a heteroelgous polynucleotide is 3' to the ENV polynucleotide and 5' to the 3' LTR. Typically, a cassette comprising the IRES or regulatory domain will be immediately downstream of the stop codon for the env gene (e.g., about 1 to 80 base pairs downstream).

In another embodiment, the disclosure provides modified retroviral vectors. The modified retroviral vectors can be derived from members of the retroviridae family. The Retroviridae family consists of three groups: the spumaviruses—(or foamy viruses) such as the human foamy virus (HFV); the lentiviruses, as well as visna virus of sheep; and the oncoviruses (although not all viruses within this group are oncogenic). The term "lentivirus" is used in its conventional sense to describe a genus of viruses containing reverse transcriptase. The lentiviruses include the "immunodeficiency viruses" which include human immunodeficiency virus (HIV) type 1 and type 2 (HIV-1 and HIV-2) and simian immunodeficiency virus (SIV). The oncoviruses have historically been further subdivided into groups A, B, C and D on the basis of particle morphology, as seen under the electron microscope during viral maturation. A-type particles represent the immature particles of the B- and D-type viruses seen in the cytoplasm of infected cells. These particles are not infectious. B-type particles bud as mature virion from the plasma membrane by the enveloping of intracytoplasmic A-type particles. At the membrane they possess a toroidal core of 75 nm, from which long glycoprotein spikes project. After budding, B-type particles contain an eccentrically located, electron-dense core. The prototype B-type virus is mouse mammary tumor virus (MMTV). No intracytoplasmic particles can be observed in cells infected by C-type viruses. Instead, mature particles bud directly from the cell surface via a crescent 'C'-shaped condensation which then closes on itself and is enclosed by the plasma membrane. Envelope glycoprotein spikes may be visible, along with a uniformly electron-dense core. Budding may occur from the surface plasma membrane or directly into intracellular vacuoles. The C-type viruses are the most commonly studied and include many of the avian and murine leukemia viruses (MLV). Bovine leukemia virus (BLV), and the human T-cell leukemia viruses types I and II (HTLV-I/II) are similarly classified as C-type particles because of the morphology of their budding from the cell surface. However, they also have a regular hexagonal morphology and more complex genome structures than the prototypic C-type viruses such as the murine leukemia viruses (MLV). D-type particles resemble B-type particles in that they show as ring-like structures in the infected cell cytoplasm, which bud from the cell surface, but the virion incorporate short surface glycoprotein spikes. The electron-dense cores are also eccentrically located within the particles. Mason Pfizer monkey virus (MPMV) is the prototype D-type virus.

Retroviruses have been classified in various ways but the nomenclature has been standardized in the last decade (see ICTVdB—The Universal Virus Database, v4 on the World Wide Web (www) at ncbi.nlm.nih.gov/ICTVdb/ICTVdB/ and the text book "Retroviruses" Eds Coffin, Hughs and Varmus, Cold Spring Harbor Press 1997; the disclosures of which are incorporated herein by reference). In one embodiment, the replication competent retroviral vector can comprise an Orthoretrovirus or more typically a gamma retrovirus vector.

The retrovirus particle is composed of two identical RNA molecules. Each wild-type genome has a positive sense, single-stranded RNA molecule, which is capped at the 5' end and polyadenylated at the 3' tail. The diploid virus particle contains the two RNA strands complexed with gag proteins, viral enzymes (pol gene products) and host tRNA molecules within a 'core' structure of gag proteins. Surrounding and protecting this capsid is a lipid bilayer, derived from host cell membranes and containing viral envelope (env) proteins. The env proteins bind to a cellular receptor for the virus and the particle typically enters the host cell via receptor-mediated endocytosis and/or membrane fusion.

After the outer envelope is shed, the viral RNA is copied into DNA by reverse transcription. This is catalyzed by the reverse transcriptase enzyme encoded by the pol region and uses the host cell tRNA packaged into the virion as a primer for DNA synthesis. In this way the RNA genome is converted into the more complex DNA genome.

The double-stranded linear DNA produced by reverse transcription may, or may not, have to be circularized in the nucleus. The provirus now has two identical repeats at either end, known as the long terminal repeats (LTR). The termini of the two LTR sequences produces the site recognized by a pol product—the integrase protein—which catalyzes integration, such that the provirus is always joined to host DNA two base pairs (bp) from the ends of the LTRs. A duplication of cellular sequences is seen at the ends of both LTRs, reminiscent of the integration pattern of transposable genetic elements. Integration is thought to occur essentially at random within the target cell genome. However, by modifying the long-terminal repeats it is possible to control the integration of a retroviral genome.

Transcription, RNA splicing and translation of the integrated viral DNA is mediated by host cell proteins. Variously spliced transcripts are generated. In the case of the human retroviruses HIV-1/2 and HTLV-I/II viral proteins are also used to regulate gene expression. The interplay between cellular and viral factors is a factor in the control of virus latency and the temporal sequence in which viral genes are expressed.

Retroviruses can be transmitted horizontally and vertically. Efficient infectious transmission of retroviruses requires the expression on the target cell of receptors which specifically recognize the viral envelope proteins, although viruses may use receptor-independent, nonspecific routes of entry at low efficiency. In addition, the target cell type must be able to support all stages of the replication cycle after virus has bound and penetrated. Vertical transmission occurs when the viral genome becomes integrated in the germ line of the host. The provirus will then be passed from generation to generation as though it were a cellular gene. Hence endogenous proviruses become established which frequently lie latent, but which can become activated when the host is exposed to appropriate agents.

As mentioned above, the integrated DNA intermediate is referred to as a provirus. Prior gene therapy or gene delivery systems use methods and retroviruses that require transcription of the provirus and assembly into infectious virus while in the presence of an appropriate helper virus or in a cell line containing appropriate sequences enabling encapsidation without coincident production of a contaminating helper virus. As described below, a helper virus is not required for the production of the recombinant retrovirus of the disclosure, since the sequences for encapsidation are provided in the genome thus providing a replication competent retroviral vector for gene delivery or therapy.

Existing replication competent retroviral vectors also tend to lose inserted heterologous sequences from an infected cell or host cell during horizontal or vertical transmission and during replication. This may be due in-part from the presence of extra nucleotide sequences that include repeats or which reduce the efficiency of a polymerase.

The retroviral genome and the proviral DNA of the disclosure have at least three genes: the gag, the pol, and the env, these genes may be flanked by one or two long terminal (LTR) repeat, or in the provirus are flanked by two long terminal repeat (LTR) and sequences containing cis-acting sequences such as psi. The gag gene encodes the internal structural (matrix, capsid, and nucleocapsid) proteins; the pol gene encodes the RNA-directed DNA polymerase (reverse transcriptase), protease and integrase; and the env gene encodes viral envelope glycoproteins. The 5' and/or 3' LTRs serve to promote transcription and polyadenylation of the virion RNAs. The LTR contains all other cis-acting sequences necessary for viral replication. Lentiviruses have additional genes including vif, vpr, tat, rev, vpu, nef, and vpx (in HIV-1, HIV-2 and/or SIV).

Adjacent to the 5' LTR are sequences necessary for reverse transcription of the genome (the tRNA primer binding site) and for efficient encapsidation of viral RNA into particles (the Psi site). If the sequences necessary for encapsidation (or packaging of retroviral RNA into infectious virion) are missing from the viral genome, the result is a cis defect which prevents encapsidation of genomic viral RNA. This type of modified vector is what has typically been used in prior gene delivery systems (i.e., systems lacking elements which are required for encapsidation of the virion).

The phrase "non-dividing" cell refers to a cell that does not go through mitosis. Non-dividing cells may be blocked at any point in the cell cycle, (e.g., $G_0/G_1$, $G_{1/S}$, $G_{2/M}$), as long as the cell is not actively dividing. For ex vivo infection, a dividing cell can be treated to block cell division by standard techniques used by those of skill in the art, including, irradiation, aphidocolin treatment, serum starvation, and contact inhibition. However, it should be understood that ex vivo infection is often performed without blocking the cells since many cells are already arrested (e.g., stem cells). For example, a recombinant lentivirus vector is capable of infecting any non-dividing cell, regardless of the mechanism used to block cell division or the point in the cell cycle at which the cell is blocked. Examples of pre-existing non-dividing cells in the body include neuronal, muscle, liver, skin, heart, lung, and bone marrow cells, and their derivatives. For dividing cells oncoretroviral or gamma retroviral vectors can be used.

By "dividing" cell is meant a cell that undergoes active mitosis, or meiosis. Such dividing cells include stem cells, skin cells (e.g., fibroblasts and keratinocytes), gametes, and other dividing cells known in the art. Of particular interest and encompassed by the term dividing cell are cells having cell proliferative disorders, such as neoplastic cells. The term "cell proliferative disorder" refers to a condition characterized by an abnormal number of cells. The condition can include both hypertrophic (the continual multiplication of cells resulting in an overgrowth of a cell population within a tissue) and hypotrophic (a lack or deficiency of cells within a tissue) cell growth or an excessive influx or migration of cells into an area of a body. The cell populations are not necessarily transformed, tumorigenic or malignant cells, but can include normal cells as well. Cell proliferative disorders include disorders associated with an overgrowth of connective tissues, such as various fibrotic conditions, including scleroderma, arthritis and liver cirrhosis. Cell proliferative disorders include neoplastic disorders such as head and neck carcinomas. Head and neck carcinomas would include, for example, carcinoma of the mouth, esophagus, throat, larynx, thyroid gland, tongue, lips, salivary glands, nose, paranasal sinuses, nasopharynx, superior nasal vault and sinus tumors, esthesioneuroblastoma, squamous call cancer, malignant melanoma, sinonasal undifferentiated carcinoma (SNUC), brain (including glioblastomas) or blood neoplasia. Also included are carcinoma's of the regional lymph nodes including cervical lymph nodes, prelaryngeal lymph nodes, pulmonary juxtaesophageal lymph nodes and submandibular lymph nodes (Harrison's Principles of Internal Medicine (eds., Isselbacher, et al., McGraw-Hill, Inc., 13th Edition, pp 1850-1853, 1994). Other cancer types, include, but are not limited to, lung cancer, colon-rectum cancer, breast cancer, prostate cancer, urinary tract cancer, uterine cancer lymphoma, oral cancer, pancreatic cancer, leukemia, melanoma, stomach cancer, skin cancer and ovarian cancer. The cell prolifereative disease also includes rheumatoid arthritis (O'Dell NEJM 350:2591 2004) and other auto-immune disorders (Mackay et al NEJM 345:340 2001) that are often characterized by inappropriate proliferation of cells of the immune system.

The term "regulatory nucleic acid sequence" or "regulatory domain" refers collectively to promoter sequences, polyadenylation signals, transcription termination sequences, upstream regulatory domains, origins of replication, enhancers and the like, which collectively provide for the replication, transcription and translation of a coding sequence in a recipient cell. Not all of these control sequences need always be present so long as the selected coding sequence is capable of being replicated, transcribed and translated in an appropriate host cell. One skilled in the art can readily identify regulatory nucleic acid sequence from public databases and materials. Furthermore, one skilled in the art can identify a regulatory sequence that is applicable for the intended use, for example, in vivo, ex vivo, or in vitro.

An internal ribosome entry sites ("IRES") refers to a segment of nucleic acid that promotes the entry or retention of a ribosome during translation of a coding sequence usually 3' to the IRES. In some embodiments the IRES may comprise a splice acceptor/donor site, however, preferred IRESs lack a splice acceptor/donor site. Normally, the entry of ribosomes into messenger RNA takes place via the cap located at the 5' end of all eukaryotic mRNAs. However, there are exceptions to this universal rule. The absence of a cap in some viral mRNAs suggests the existence of alternative structures permitting the entry of ribosomes at an internal site of these RNAs. To date, a number of these structures, designated IRES on account of their function, have been identified in the 5' noncoding region of uncapped viral mRNAs, such as that, in particular, of picornaviruses such as the poliomyelitis virus (Pelletier et al., 1988, Mol. Cell. Biol., 8, 1103-1112) and the EMCV virus (encephalomyocarditis virus (Jang et al., J. Virol., 1988, 62, 2636-2643). The disclosure provides the use of an IRES in the context of a replication-competent retroviral vector.

The term "promoter region" is used herein in its ordinary sense to refer to a nucleotide region comprising a DNA regulatory sequence, wherein the regulatory sequence is derived from a gene which is capable of binding RNA polymerase and initiating transcription of a downstream (3'-direction) coding sequence. The regulatory sequence may be homologous or heterologous to the desired gene sequence. For example, a wide range of promoters may be utilized, including viral or mammalian promoter as described above.

In one embodiment, the RRV genome is derived from an onco-retrovirus or gamma-retrovirus, and more particularly a mammalian onco-retrovirus or gamma-retrovirus. By "derived" is meant that the parent polynucleotide sequence is an wild-type oncovirus which has been modified by insertion or removal of naturally occurring sequences (e.g., insertion of an IRES, insertion of a heterologous polynucleotide encoding a polypeptide or inhibitory nucleic acid of interest, swapping of a more effective promoter from a different retrovirus or virus in place of the wild-type promoter and the like).

The following Examples are intended to illustrate, but not to limit the disclosure. While such Examples are typical of those that might be used, other procedures known to those skilled in the art may alternatively be utilized.

EXAMPLES

Drugs and Reagents

TMZ (brand names: Temodar or Temodal) for in vitro assays was purchased from Sigma (St Louis, Mo., USA); Temodar for in vivo studies were purchased from Merck (Whitehouse Station, N.J., USA). 5-FC for both in vitro and in vivo assays was purchased from Nantong Jinghua Pharmaceutical Company (Nantong, Jiangsu, China).

Toca 511.

A detailed description of Toca 511 vector design and modification has been described previously (Perez O D, Logg C R, Hiraoka K, Diago O, Burnett R, Inagaki A et al. Design and selection of toca 511 for clinical use: modified retroviral replicating vector with improved stability and gene expression. Mol Ther 2012; 20: 1689-1698). Briefly, modifications were made to the plasmid pACE-green fluorescent protein (GFP) (Logg et al., J. Virol, 75:6969-6998, 2001) to improve stability and increase convenience of transgene insertion to yield the vector pAC3-GFP. Genetic enhancements to the wild-type yeast CD gene were made as follows: (1) the codon usage was optimized for protein synthesis in human cells; and (2) three amino-acid changes were introduced (A23L, I140L and V108I) to increase thermal stability of the yeast CD protein. The plasmid pAC3-yCD2 was generated by substituting the modified CD gene into pAC3-GFP. Toca 511 is the vector produced from this plasmid using the production and formulation methods developed for clinical use.

Cell Culture.

Human glioma cell lines U-87MG (ATCC, Manassas, Va., USA; HTB-14), LN-18 (ATCC; CRL-2610), LN-229 (ATCC; CRL-2611), 8-MG-BA,15 and the mouse glioma cell line Tu-2449 were cultured in Dulbecco's modified Eagle's medium with 10% fetal bovine serum, sodium pyruvate and glutamax (Hyclone, Rockford, Ill., USA and Invitrogen, Grand Island, N.Y., USA). Cells were maintained in a humidified atmosphere with 5% $CO_2$ at 37° C. When ready for in vivo implantation, cells were resuspended in Dulbecco's modified Eagle's medium media without any additives.

MGMT Protein Detection Assay.

Cells were lysed in ice-cold lysis buffer (0.5 mmol ethylenediaminetetraacetic acid, 150 mmol NaCl, 10 mmol Tris-HCl (pH 7.4), 0.5% NP-40, 0.5% sodium dodecyl sulfate, 0.1% sodium deoxycholate) supplemented with protease inhibitor cocktail (Sigma) for 15 min on ice followed by passing through a 27-G needle five times. Lysates were centrifuged at 13 000 r.p.m. for 20 min at 4° C. Protein concentrations of cell lysates were measured according to Bradford assay. Ten micrograms of protein was separated on sodium dodecyl sulfate-poly-acrylamide gel electrophoresis using NuPAGE 4-12% gradient gel (Invitrogen), and transferred onto the polyvinylidene fluoride membrane (GE Healthcare, Pittsburgh, Pa., USA). Mouse monoclonal antibodies to human MGMT protein (Abcam, Cambridge, Mass., USA) and to b-actin (Abcam) were used as primary antibody. Horse radish peroxidase-conjugated rabbit antimouse monoclonal antibody (Dako, Carpinteria, Calif., USA) was used as the secondary antibody.

Clonogenic Assay.

Briefly, 500 cells were seeded in 6-cm tissue culture dishes. After an overnight incubation, cells were treated with different concentrations of TMZ (Sigma) in Dulbecco's modified Eagle's mediump10% fetal calf serum. Cells were cultivated for 10 days without replacing the medium, and thereafter washed with phosphate-buffered saline (PBS) and stained using May-Grunwald staining solution (Sigma). Colonies containing more than 40 cells were manually counted. The results are reported as a percentage of the colonies in untreated cultures of each corresponding cell line. At least three independent experiments using each cell line were performed. The data are expressed as means±s.e.m.

In Vitro RRV-GFP Spread.

Two different TMZ schedules were tested. To test the effect of preincubation with TMZ, cells were seeded at a density of $1\times10^5$ cells per well on six-well plates. After 24 h, different concentrations of TMZ were added to the cells. The next day, cells were infected with RRV-GFP vector at a multiplicity of infection of 0.1. To test the effect of concomitant TMZ, cells were seeded at a density of $1\times10^5$ cells per well on six-well plates. After 48 h, cells were infected with RRV-GFP vector at a multiplicity of infection of 0.1 in the presence of different concentrations of TMZ. The following day, cells were transferred to T25 flasks keeping the indicated TMZ concentration. Cells were analyzed three times a week by enhanced green fluorescent protein fluorescence-activated cell sorting analysis for virus spread, maintaining the indicated TMZ concentration during the entire experiment.

In Vitro 5-FC Sensitivity Assay.

Tu-2449 and U-87MG cells were infected with ~$1\times10^4$ transducing units (TU) $ml^{-1}$ of Toca 511 in the presence of polybrene (8 $mgml^{-1}$). Cells were passaged 2-3 times a week for 17 days. Fluorescence-activated cell sorting-based analysis of 4070A envelope (indicating Toca 511-infected cells) performed before sensitivity testing of these cells revealed that 89-99% of cells were infected. Cells were seeded on day 0 at a concentration of $1\times10^3$ cells per well of a 96-well plate in 80 ml of culture medium (Dulbecco's modified Eagle's mediump10% fetal calf serum+gentamicin (17 mg per 100 ml)). On day 1, 20 ml of culture medium containing 5-FC (range 0-1000 $mgml^{-1}$), TMZ (range 0-100 $mgml^{-1}$) or both drugs (5-FC (range 0-1.6 $mgml^{-1}$) and TMZ (2 $mgml^{-1}$)) was added to the cells. Viability was measured on day 6 using Cell Proliferation Kit II (XTT) (Roche, Indianapolis, Ind., USA) as recommended by the manufacturer.

Mice and Intracranial Surgeries.

Female B6C3F1 or athymic nude-Foxn1^nu mice (age ~8 weeks) were purchased from Harlan (Indianapolis, Ind., USA or Udine, Italy). Mice were acclimated for 3-7 days after arrival. Mice underwent surgical placement of an indwelling guide cannula with a 3.0 mm projection implanted into the right striatum, and fitted with a cap containing a 3.5 mm projection for the Tu-2449 in vivo studies. Mice underwent surgical implantation of the tumor cells by Hamilton syringe for the U-87MG in vivo studies. The stereotaxic coordinates for both studies were AP=0.5 mm, ML=1.8 mm and DV=3.5 mm (from bregma).

In Vivo Survival Studies.

The syngeneic cell line Tu-2449 was used as an orthotopic brain tumor model in B6C3F1 mice. Cell implantation and vector/vehicle injections were through an injection cannula with a 3.5 mm projection inserted through the guide cannula. B6C3F1 mice underwent intracranial implantation of $1.4 \times 10^4$ tumor cells on day 0. On day 4, mice were injected with Toca 511 (3.15E4 TU $g^{-1}$) or vehicle control (IC; 5 ml per mouse) by intracranial infusion at 0.33 ml min (15 min, followed by a hold of 5 min). Starting on day 10, mice were treated with either PBS or 5-FC (500 mgkg$^{-1}$ per dose, i.p., b.i.d.) for 4 consecutive days, followed by 10 days without drug to allow vector spread. Cycles of 4-day on, 10-day off drug treatment were repeated three more times. In one set of studies, TMZ (25 mgkg$^{-1}$ per day, i.p., semel in die (SID) once a day) was administered on day 4 (the day of vector/vehicle injection) for 4 consecutive days, and then followed the 5-FC/PBS dosing schedule for four cycles. In the other set of studies, TMZ (25 mgkg$^{-1}$ per day, i.p.) SID was administered on the same days as the 5-FC/PBS treatments for four cycles.

The human malignant glioma cell line U-87MG was used as an orthotopic xenograft model in athymic nude mice. Cell implantation and vector/vehicle injections were carried out using a Hamilton syringe on a stereotaxic frame. Athymic nude mice underwent intracranial implantation of $2 \times 10^5$ tumor cells on day 0. On day 7, mice were injected with Toca 511 (3.4E4 TU $g^{-1}$) or vehicle control (IC; 5 ml per mouse for 10 min, followed by a hold of 5 min). Starting on day 14, mice were treated with either PBS or 5-FC (500 mgkg$^{-1}$ per day) IP SID for 4 consecutive days, followed by 10 days without drug to allow vector spread. Cycles of 4-day on, 10-day off 5-FC drug treatment were repeated three more times. TMZ (25 mgkg$^{-1}$ per day, intraperitoneally, SID) was administered on the same days as the 5-FC/PBS treatments for four cycles. All surviving mice were killed on day 180 after glioma cell injection.

Two different lots of Toca 511 were used for all in vivo studies. Toca 511 lot T511015-FNL had a starting titer of $1.7 \times 10^8$ TU ml$^{-1}$, whereas Toca 511 lot T511082-FNL had a starting titer of $6.3 \times 10^8$ TU ml$^{-1}$. Toca 511 doses are defined as TU g$^{-1}$ of brain, with the average mouse brain defined as 0.5 g.

In-Life Observations.

Routine general health, in-life observations and body weights were collected throughout the course of the study. In-life observations were scored on a 0-4 point system for severity of each symptom. Mice with a cumulative score of 5 were euthanized. Mice with body weight loss of >20% for more than 2 days were euthanized. All animal protocols and experiments were approved by either the Institutional Animal Care and Use Committee (A4487-01) of Explora (San Diego, Calif., USA) or the University of Veterinary Medicine Ethics Committee and Austrian government authorities (BMWF-68.205/0163-II/3b/2010; BMWF-68.205/0151-II/3b/2011).

Statistical Analyses.

Survival data were plotted using the Kaplan-Meier method, and were compared by the log-rank test or Student's t-test as noted. P-values of <0.05 were considered statistically significant in all analyses, which were carried out with Prism 5 statistical software (GraphPad Software, La Jolla, Calif., USA).

Determination of TMZ Sensitivity in Glioma Cells.

The presence of MGMT protein in tumor cells has been shown to render them less susceptible to TMZ treatment. A panel of glioma cells, including human glioma cell lines (U-87MG, LN-18, LN-229, 8-MG-BA) and a mouse glioma cell line (Tu-2449), were examined for their sensitivity to TMZ. First, protein expression of MGMT was determined in the four human glioma cell lines, and LN-18 was the only line that expressed visible MGMT protein level on immunoblot (FIG. 1a). Further examination of the sensitivity by clonogenic assay with different concentrations of TMZ in all five glioma cells demonstrated that U-87MG, LN-229 and 8-MG-BA cell lines were very sensitive to TMZ at the lowest concentration tested (2 mgml$^{-1}$) consistent with the lack of MGMT protein expression (FIG. 1b). LN-18, the human glioma cell line that expressed MGMT protein, was confirmed to be more resistant to TMZ up to a concentration of 100 mgml$^{-1}$. The mouse glioma cell line Tu-2449 was also resistant to TMZ up to a concentration of 100 mgml$^{-1}$ (FIG. 1b).

Treatment with TMZ does not Inhibit RRV-GFP Spread in Glioma Cells In Vitro.

Figure 2:
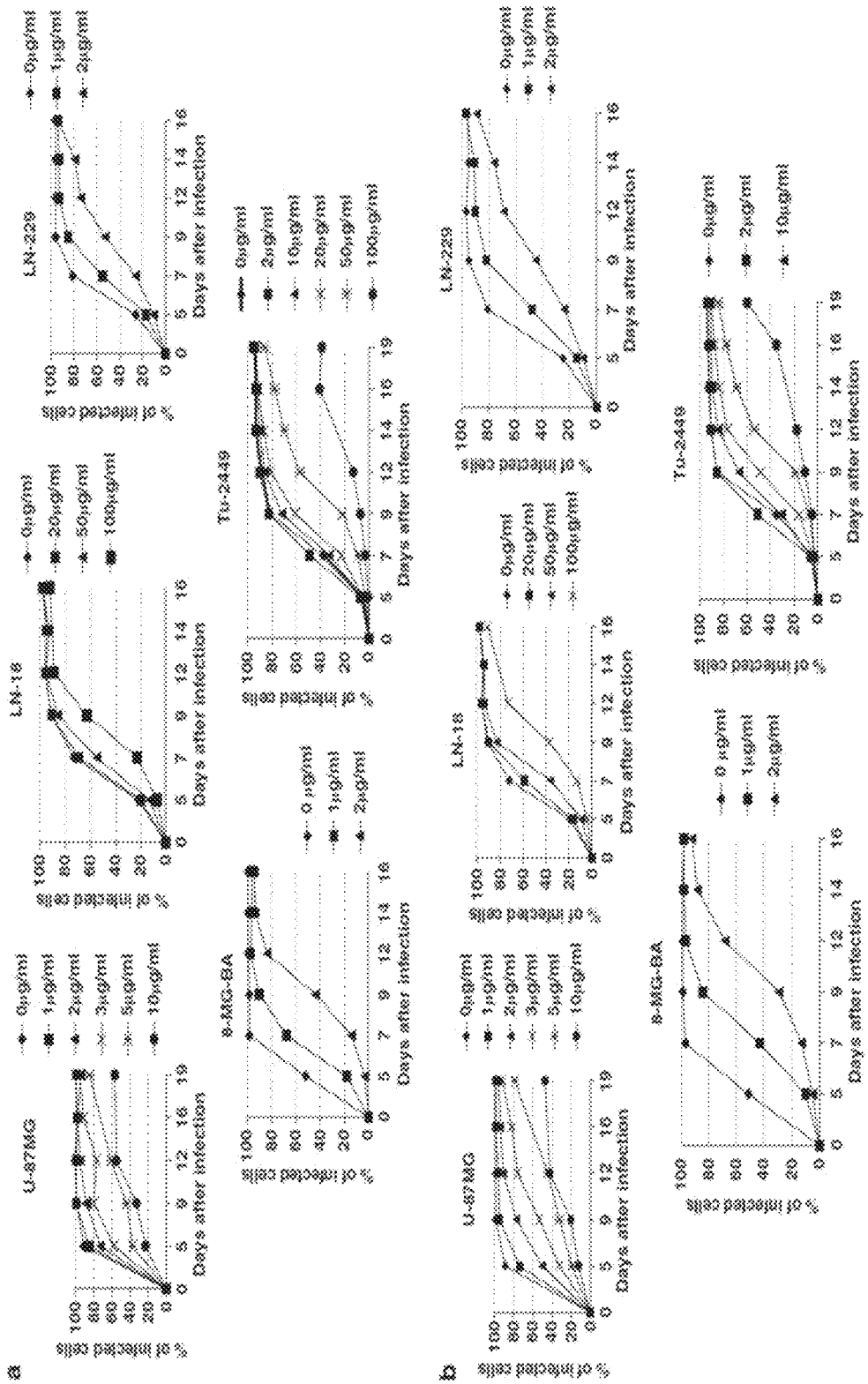
FIG. 2A-B shows that treatment with non-toxic temozolomide (TMZ) levels does not inhibit retroviral replicating vector-green fluorescent protein (RRV-GFP) spread in glioma cells. Five glioma cell lines were tested for infection with RRV-GFP after treatment with various concentrations of TMZ at two different schedules (A). Twenty-four hours before initial RRV-GFP infection, and (B) concomitantly with initial RRV-GFP infection. Cells were collected at different time points (indicated on the x axis) to check for the percentage of GFP-positive cells by fluorescence activated cell sorter analysis.

To test any possible effect of TMZ on the spread of Toca 511, the same panel of glioma cells was treated with different concentrations of TMZ depending on the TMZ sensitivity of the cells determined in the clonogenic assay in FIG. 1b. In addition, vector with the same backbone as Toca 511 but encoding a GFP transgene (RRV-GFP) was used to assess vector spread by fluorescence-activated cell sorting analysis. Two TMZ treatment schedules were tested. The first schedule tested treatment with varying concentrations of TMZ before and during the time of vector infection, and the second schedule tested treatment with varying concentrations of TMZ at the same time as the addition of vector. In the first schedule, glioma cells were incubated with different concentrations of TMZ 24 h before the addition of RRVGFP at a multiplicity of infection of 0.1. As shown in FIG. 2a, all five glioma cells reached nearly 100% GFP positivity by day 12 without TMZ, indicating that the cells were susceptible to RRV-GFP infection. LN-229 and 8-MG-BA, two glioma cells that are most sensitive to TMZ in the panel (FIG. 1b), showed a delayed infectivity with 1 and 2 mgml$^{-1}$ of TMZ compared with no TMZ control; however, the cells eventually reached 100% GPF positivity by day 16. There was an initial lag or decrease in GFP positivity at earlier time points (FIG. 2a). U-87MG cells also displayed a delayed infectivity with up to 5 mgml$^{-1}$ of TMZ, whereas 10 mgml$^{-1}$ of TMZ killed nearly 90% of the cells (FIGS. 2a and 1b). Two relatively TMZ-resistant glioma cell lines, LN-18 and Tu-2449, at TMZ concentration up to 20 mgml$^{-1}$, also showed a pattern of delayed infectivity, but reached nearly 100% of GFP positivity by day 19 (FIG. 2a). TMZ at 50 mgml$^{-1}$ or higher reduced infectivity in Tu-2449 cell line. In the second schedule, when TMZ and RRV-GFP were added to the glioma cells concomitantly, the same trend was observed; after an initial lag, cells reached nearly 100% GFP positivity in the presence of TMZ (FIG. 2b). The observed infectivity lag was likely due to induction of apoptosis in a certain percentage of cells with TMZ treatment. Surviving cells were still susceptible to infection with RRV-GFP and able to produce more RRV-GFP virus for further infection and spread within the culture dish. TMZ treatment, either before or concomitantly with RRV-GFP infection, did not inhibit vector spread in glioma cells in vitro, regardless of the cells' sensitivity to TMZ. Rather the data is consistent with the conclusion that slowing of tumor cell replication with the anticancer drug TMZ, slows the replication of the RRV because of the inhibition of cancer cell replication and the requirement for cell replication for productive infection with RRV.

Treatment with TMZ does not Inhibit Toca 511+5-FC Killing of Glioma Cells In Vitro.

Figure 3:
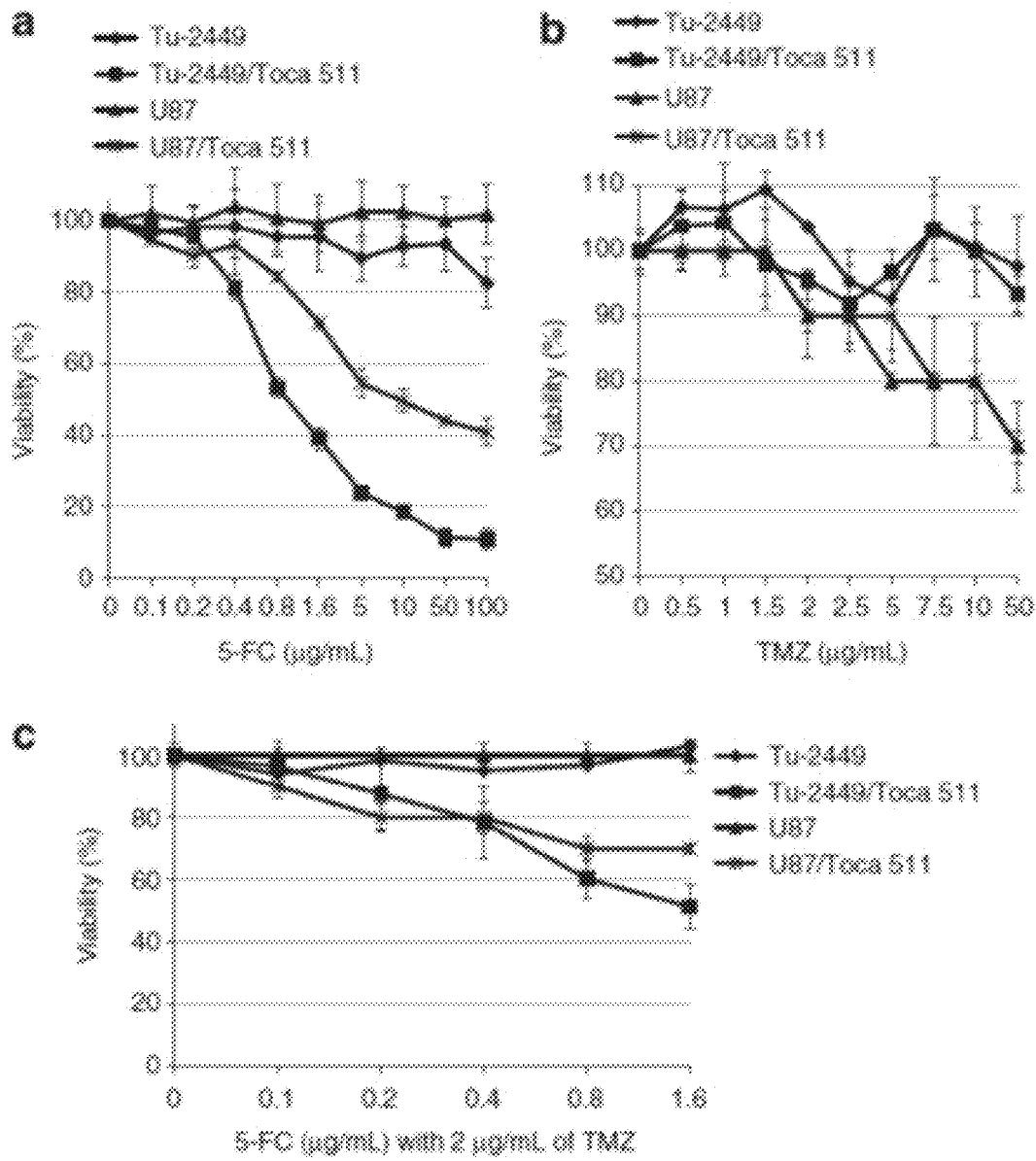
FIG. 3A-C shows treatment with temozolomide (TMZ) does not inhibit Toca 511+5-fluorocytosine (5-FC) treatment in glioma cells in vitro. U-87MG and Tu-2449 cells (naive and Toca 511 pretransduced) treated with (A) 5-FC alone (0-1000 μg ml$^{-1}$), (B) TMZ alone (0-100 μg ml$^{-1}$) and (C) 5-FC (0-1.6 μg ml$^{-1}$) and TMZ (2 μg ml$^{-1}$) combination.

Previous studies have shown that intratumoral administration of Toca 511 in combination with 5-FC treatment resulted in prolonged survival in mouse brain tumor models. Two glioma lines U-87MG (TMZ-sensitive) and Tu-2449 (TMZ-resistant) were chosen to examine the compatibility of TMZ and Toca 511p5-FC treatment in previously infected cells. These two cell lines were cultured as either non-transduced control or 100% Toca 511-transduced cells. Sensitivity to 5-FC was examined by measuring cell viability after culture in increasing amounts of 5-FC. Both naive (non-transduced) cell lines were highly resistant to 5-FC (up to 100 mgml$^{-1}$), and the two Toca 511-transduced cells were sensitive to 5-FC in a dose-dependent manner (FIG. 3a). In addition, cell viability was examined in the nontransduced and transduced cell lines treated with increasing amounts of TMZ. Consistent with results from FIG. 1b, U-87MG cells were sensitive to TMZ and Tu-2249 cells were relatively resistant to TMZ (FIG. 3b). The Toca 511-transduced cells also followed the same trend as the naive cells in TMZ sensitivity; in addition, the expression of the transgene CD protein from Toca 511-transduced glioma cells did not affect the cells' sensitivity to TMZ (FIG. 3b). When these cells were treated with a combination of TMZ (2 mgml$^{-1}$) and 5-FC (titrating amounts) concomitantly, the data showed that TMZ did not inhibit 5-FC killing in Toca 511-transduced cells, regardless of their TMZ sensitivity (FIG. 3c).

Negative Impact on the Therapeutic Effect of Toca 511+5-FC when TMZ was Administered During the Initial Vector Infection and Spread in a TMZ-Resistant Orthotopic Glioma Cell Model.

Figure 4:
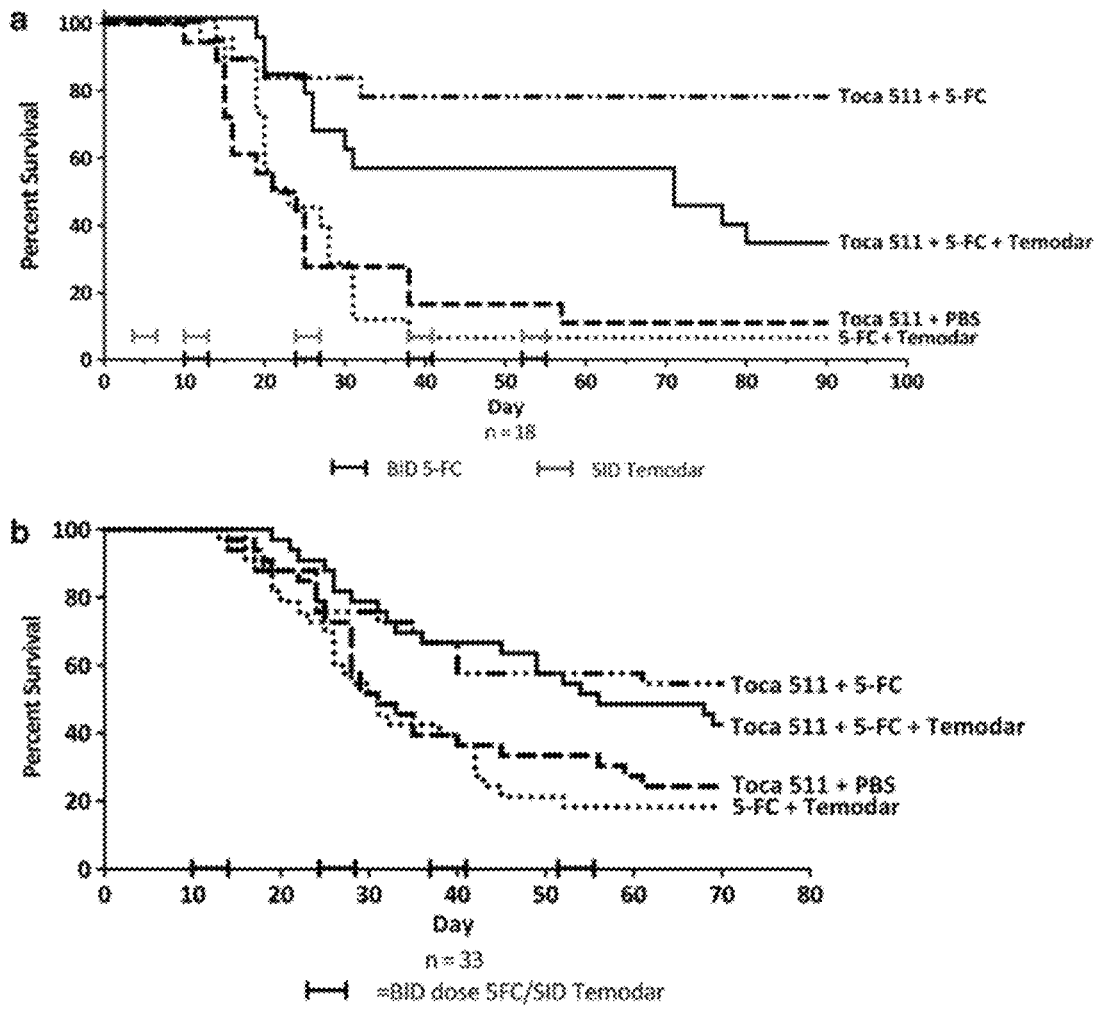
FIG. 4A-B shows combination of temozolomide (TMZ) and Toca 511+5-fluorocytosine (5-FC) treatment following Toca 511 administration and spread demonstrates no inhibitory effect on efficacy in a TMZ-resistant Tu-2449 mouse glioma orthotopic model in syngeneic mice. Two different TMZ treatment schedules were tested. (A) TMZ was administered throughout the experiment, including during the initial Toca 511 infection and spread (days 4-7), and concomitantly with the 5-FC treatment. (B) TMZ was given concomitantly with the 5-FC treatment only. Four cycles of 5-FC treatment (4-day on, 10-day off) were given to mice and survival was examined out to 90 (A) or 70 days (B).

A dose finding study was conducted in healthy B6C3/F1 hybrid mice to evaluate the clinical effects and possible hematological changes during concomitant administration of 5-FC and TMZ. Both drugs are known to cause hematological toxicity in some circumstances and therefore it is important to examine any potential drug interaction with respect to this potentially toxic side effect. Three concentrations of TMZ (25, 60 and 125 mgkg$^{-1}$) in combination with a fixed dose of 5-FC (500 mgkg$^{-1}$ per dose) were administered intraperitoneal SID for 4 consecutive days starting on days 1, 8, 22 and 36. Mice were terminated on day 51 for hematological examination. TMZ at 25 mgkg$^{-1}$ per day (human equivalent of 75 mgm$^{-2}$) could be safely administered to the mice without significant hematological changes. The highest TMZ dose (125 mgm$^{-2}$) when coadministered with 5-FC resulted in significant reduction in platelet counts and almost complete loss of leukocytes (Table 1).

shown that this model displays several of the features of human glioblastoma, and is highly angiogenic. Tu-2449 glioma cells were implanted intracranially into syngeneic B6C3/F1 mice (n=18 per treatment group), and Toca 511 (3.15E4 TU g$^{-1}$) or vehicle control was administered once intratumorally 4 days after tumor implant. Mice were also given TMZ treatment (25 mgkg$^{-1}$ per day, intraperitoneally, SID) starting on the same day as the vector injection for 4 consecutive days (days 4-7). Mice were treated again with TMZ (25 mgkg$^{-1}$ per day, intraperitoneally, SID), and 5-FC (500 mgkg$^{-1}$ per day, intraperitoneally, twice a day) or PBS on days 10-13. Both drugs were administered for 4 consecutive days, followed by 10 days without drug to allow more vector spread. Cycles of the TMZ±5-FC treatment were repeated three times (starting on days 24, 38 and 52). All surviving mice were killed on day 90 after glioma cell implantation (FIG. 4a).

No treatment-related effects on body weight were observed during the study. There were no treatment-related differences in incidence of in-life observations across groups through day 90. Mice with large tumor burden, regardless of treatment group, showed weight loss and increased hunching and lethargy. Treatment of Toca 511+5-FC (intraperitoneally, twice a day) with or without TMZ resulted in statistically prolonged survival compared with the control group (Toca 511±PBS), with a median survival of 22.5 days (P-values=0.0001 and 0.0088, respectively). Treatment of mice with Toca 511+5-FC (intraperitoneally, twice a day) with TMZ resulted in statistically prolonged survival compared with the TMZ control group (buffer±TMZ±5-FC, intraperitoneally, twice a day), with a median survival of 71 and 22 days, respectively (P-value=0.004). However, mice treated with Toca 511+5-FC (intraperitoneally, twice a day) and TMZ during Toca 511 treatment and spread (days 4-7) had a decreased survival rate compared with mice treated with Toca 511+5-FC (intraperitoneally, twice a day) (P-value=0.0176) (FIG. 4a). The median survival in this group was not determined as >50% of the animals survived to the end of the experiment. These results indicate TMZ in combination with Toca 511+5-FC treatment had a negative impact on the therapeutic effect of Toca 511+5-FC (intraperitoneally, twice a day) treatment when TMZ was administered during the initial vector infection and spread period.

Combination of TMZ and 5-FC Treatment Shows Equivalent Efficacy to 5-FC Alone in a TMZ-Resistant Orthotopic Glioma Model, when Administered after Toca 511 Infection and Spread.

TABLE 1

Mean blood values for B6C3/F1 mice (Day 51)

| | Hematocrit % | Leukocytes/μl | Platelets/μl | Creatinine mg/dl | ALT U/L |
|---|---|---|---|---|---|
| Group 1 PBS | 39 | 2818 | 682400 | 0.37 | 39 |
| Group 2 5-FC + TMZ 25 mg/kg (75 mg/m$^2$) | 38 | 1951 | 751800 | 0.36 | 41 |
| Group 3 5-FC + TMZ 60 mg/kg (200 mg/m$^2$) | 38 | 1489 | 730400 | 0.35 | 36 |
| Group 4 5-FC + TMZ 125 mg/kg (400 mg/m$^2$) | 16 | 0.26 | 123250 | 0.25 | 24 |

To test the effect of the combination therapy of TMZ and Toca 511+5-FC treatment in a TMZ-resistant cell line in vivo, the Tu-2449 mouse glioma cell line was chosen as this line has been used as an orthotopic, syngeneic mouse glioma model in B6C3/F1 hybrid mice. Previous studies have A different TMZ dosing schedule was implemented in a new study to further investigate the effect of TMZ in Toca 511+5-FC treatment in the Tu-2449 TMZ-resistant glioma line. Tu-2449 mouse glioma cells were implanted intracranially into the syngeneic B6C3F1 mice (n=33 per treatment group), and Toca 511 (3.15E4 TU $g^{-1}$ brain) or vehicle control was administered intratumorally 4 days after tumor implant. However, TMZ was not administered during the initial vector infection and spread period (days 4-7) unlike the previous study. Five days after vector injection, mice were treated with TMZ (25 mgkg$^{-1}$ per day, intraperitoneally, twice a day), 5-FC (500 mgkg$^{-1}$ per day, intraperitoneally, twice a day) or PBS. Drugs were administered over 4 consecutive days followed by 10 days without drug to allow more vector spread. Cycles of the drug treatment were repeated three more times (starting on days 24, 38 and 52). All surviving mice were killed on day 70 after glioma cell implantation (FIG. 4b).

As in the previous study, no treatment-related effects on body weight or clinical observations were observed during the study. Mice with large tumor burden, regardless of treatment group, showed weight loss and increased hunching and lethargy. Treatment of Toca 511+5-FC (intraperitoneally, twice a day) with or without TMZ resulted in statistically prolonged survival compared with the control group (Toca 511±PBS) (P-values=0.05 and 0.02, respectively). Treatment of mice with Toca 511+5-FC (intraperitoneally, twice a day) with TMZ resulted in statistically prolonged survival compared with the TMZ control group (buffer±TMZ±5-FC, intraperitoneally, twice a day), with a median survival of 56 and 31 days, respectively (P value=0.004). Furthermore, mice treated with Toca 511+5-FC (intraperitoneally, twice a day) with TMZ resulted in similar survival compared with mice treated with Toca 511+5-FC (intraperitoneally, twice a day) with an undefined median survival exceeding 70 days (P value ¼0.55) (FIG. 4b). These results indicate that TMZ in combination with Toca 511+5-FC treatment does not have an inhibitory effect on the therapeutic effect of Toca 511+5-FC (intraperitoneally, twice a day) treatment in a TMZ-resistant glioma model when TMZ was not administered during the initial period of vector infection and spread.

Combination of TMZ and 5-FC Improves Long-Term Efficacy Compared with 5-FC Alone in a TMZ-Sensitive Orthotopic Glioma Model, when Administered after Toca 511 Infection and Spread.

To test the effect of the combination therapy of TMZ and Toca 511+5-FC treatment in a TMZ-sensitive cell line in vivo, the U-87MG cell line was used in an orthotopic xenograft glioma model in immunocompromised mice. A similar TMZ dose finding study as for the C3B6F1-immunocompetent mice was conducted in healthy athymic mice to evaluate the clinical effects and possible hematological changes during concomitant administration of 5-FC and TMZ. Two concentrations of TMZ (25 and 60 mgkg$^{-1}$) in combination with a fixed dose of 5-FC (500 mgkg$^{-1}$ per dose) were administered intraperitoneal SID for 4 consecutive days starting on days 1, 15, 29 and 43. Mice were terminated on day 53 for hematological examination.

TMZ at a dose of 60 mgkg$^{-1}$ (human equivalent of 200 mgm$^{-2}$) in combination with 5-FC led to substantially severe hematological changes (leukocytopenia, thrombocytopenia) and to a five fold increase in ALT activity. In contrast, the lower TMZ dose of 25 mgkg$^{-1}$ (human equivalent of 75 mgm-2, which is the dose used during first-line radiation therapy) led to mild changes in hematological parameters (Table 2).

TABLE 2

Mean blood values for athymic nude mice (Day 53

| | Hematocrit % | Leukocytes/µl | Platelets/µl | Creatinine mg/dl | ALT U/L |
|---|---|---|---|---|---|
| Group 1 PBS | 39 | 4492 | 648000 | 0.12 | 34 |
| Group 2 5-FC 500 mg/kg + TMZ 25 mg/kg (75 mg/m²) | 37 | 2102 | 519000 | 0.1 | 65 |
| Group 3 5-FC 500 mg/kg + TMZ 60 mg/kg (200 mg/m²) | 29 | 240 | 177000 | 0.1 | 112 |

U-87MG cells were implanted intracranially into athymic mice, and Toca 511 (3.4E4 TU g) or NaCl were injected intratumorally 7 days after tumor implantation. Treatment with TMZ (25 mgkg$^{-1}$ per day, intraperitoneally, SID), 5-FC (500 mgkg$^{-1}$ per day, intraperitoneally, SID) or PBS was initiated on day 14 to allow 6 days for initial vector infection and spread. Both drugs were administered for 4 consecutive days, followed by 10 days without drug to allow more vector spread. Cycles of the treatment were repeated three times (starting on days 28, 42 and 56). All surviving mice were killed on day 180 after glioma cell implantation.

Figure 5:
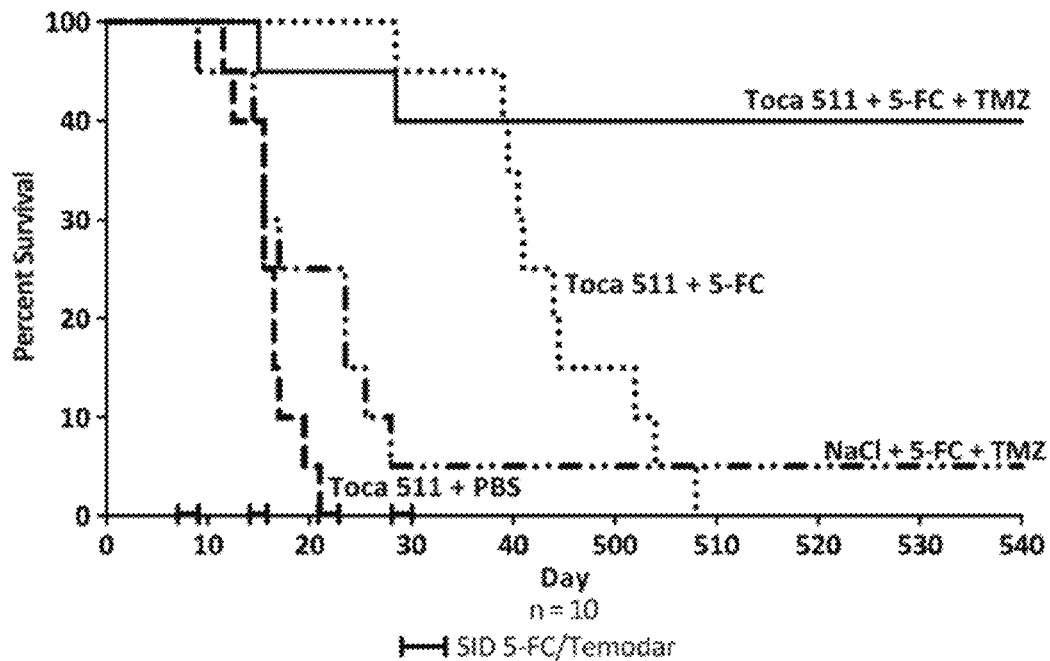
FIG. 5 shows a combination of temozolomide (TMZ) and Toca 511+5-FC treatment demonstrates synergistic efficacy in a TMZ-sensitive U-87MG human glioma orthotopic xenograft model in nude mice.

Mice treated with Toca 511+5-FC showed an increase in median survival (85 days) compared with the Toca 511±PBS control mice (32 days) (P-value<0.0001) (FIG. 5). Mice treated with Toca 511+5-FC in combination with lower dose TMZ showed a significant increase in survival compared with the no vector, 5-FC±lower dose TMZ control mice, with a median survival of undefined and 40.5 days, respectively (P-value=0.001) (FIG. 5). In addition, mice treated with Toca 511+5-FC in combination with lower dose TMZ resulted in significantly prolonged survival compared with the Toca 511+5-FC group (P-value=0.001). These results demonstrate a synergistic efficacy when combining lower dose TMZ with Toca 511+5-FC treatment in a TMZ-sensitive glioma mouse model.

What is claimed is:

1. A method of treating a cancer, said method comprising administering to the cancer a replication competent mammalian oncoretroviral vector containing a therapeutic cassette, the therapeutic cassette comprising a gene encoding a polypeptide having prodrug-activating activity, wherein the vector infects the cancer cells and wherein the cancer cells expresses the gene encoding the polypeptide; and within about 5 days to about 12 weeks after administering the vector administering a prodrug and administering separately temozolomide, wherein the prodrug is 5-fluorocytosine.

2. A method of treating a cancer in a subject, comprising administering to the subject that is free of any chemotherapeutic agents a replication competent mammalian oncoretroviral vector containing a therapeutic cassette, the therapeutic cassette comprising a gene encoding a polypeptide having cytosine deaminase activity, allowing the vector to infect cancer cells of the cancer and spread, wherein the cancer cells expresses the gene encoding the polypeptide; and within about 5 to about 20 days after administering the vector administering 5-fluorocytosine and one or more chemotherapeutic radio-sensitizing agents.

3. The method of claim 1 or 2, wherein the cancer is glioblastoma multiforme.

4. The method of claim 3, wherein the glioblastoma multiforme is recurrent glioblastoma multiforme.

5. The method of claim 1, wherein temozolomide is administered in a plurality of 28-day cycles, each cycle comprising administration of a dose of about 50 to 150 mg/m$^2$ per day each day for at least days 1-5.

6. The method of claim 1 or 2, wherein prior to administration of the vector, the cancer is resected.

7. The method of claim 1, further comprising administering radiation to the subject at the cancer site within 1-5 days of administration of 5-FC and/or temozolomide.

8. The method of claim 1 or 2, wherein the subject has not been treated with an agent that inhibits a mis-match repair process in the subject's cells.

9. The method of claim 1 or 2, wherein the cancer is selected from the group consisting of lung cancer, colon-rectum cancer, breast cancer, prostate cancer, urinary tract cancer, uterine cancer, brain cancer, head and neck cancer, pancreatic cancer, melanoma, stomach cancer and ovarian cancer.

10. The method of claim 1 or 2, wherein replication competent retrovirus comprises:
   a retroviral GAG protein;
   a retroviral POL protein;
   a retroviral envelope;
   a retroviral polynucleotide comprising Long-Terminal Repeat (LTR) sequences at the 3' end of the retroviral polynucleotide sequence, a promoter sequence at the 5' end of the retroviral polynucleotide, said promoter being suitable for expression in a mammalian cell, a gag nucleic acid domain, a pol nucleic acid domain and an env nucleic acid domain;
   a therapeutic cassette comprising a regulatory domain operably linked to a heterologous gene encoding a polypeptide having cytosine deaminase activity, wherein the cassette is positioned 5' to the 3' LTR and 3' to the env nucleic acid domain encoding the retroviral envelope; and
   cis-acting sequences necessary for reverse transcription, packaging and integration in a target cell.

11. The method of claim 10, wherein the retroviral polynucleotide sequence is derived from murine leukemia virus (MLV), Moloney murine leukemia virus (MoMLV), Feline leukemia Virus or Gibbon ape leukemia virus (GALV).

12. The method of claim 11, wherein the MLV is an amphotropic MLV.

13. The method of claim 10, wherein the retrovirus is a gammaretrovirus.

14. The method of claim 1, wherein the polypeptide has cytosine deaminase activity.

* * * * *